United States Patent
Spielmann et al.

(10) Patent No.: US 7,745,589 B1
(45) Date of Patent: Jun. 29, 2010

(54) ANTIBODIES AND UNNATURAL SUBSTRATES OF PRENYLATION ENZYMES FOR USE IN DETECTING AND ISOLATING PRENYLATED PROTEINS

(75) Inventors: Hans Peter Spielmann, Lexington, KY (US); Douglas A. Andres, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 845 days.

(21) Appl. No.: 11/459,299

(22) Filed: Jul. 21, 2006

Related U.S. Application Data

(60) Provisional application No. 60/701,162, filed on Jul. 21, 2005.

(51) Int. Cl.
 C07K 16/00 (2006.01)
(52) U.S. Cl. ............... 530/389.8; 530/388.9; 424/175.1
(58) Field of Classification Search ....................... None
 See application file for complete search history.

(56) References Cited

OTHER PUBLICATIONS

Campbell, A (Laboratory Techniques in Biochemistry and Molecular Biology, vol. 13, Chapter 1, pp. 1-33, 1984).*
Andres, D. A., Crick, D. C., Finlin, B. S., and Waechter, C. J. (1999) Rapid identification of cysteine-linked isoprenyl groups by metabolic labeling with [3H]farnesol and [3H]-geranylgeraniol. Methods Mol. Biol. 116, 107-23.
Baron, R., Fourcade, E., Lajoie-Mazenc, I., Allal, C., Couderc, B., Barbaras, R., Favre, G., Faye, J. C., and Pradines, A. (2000) RhoB prenylation is driven by the three carboxyl-terminal amino acids of the protein: evidence in vivo by an anti-farnesyl cysteine antibody. Proc. Natl. Acad. Sci. U.S.A. 97, 11626-31.
Berndt, P., Fields, G. B., and Tirrell, M. (1995) Synthetic Lipidation of Peptides and Amino Acids: Monolayer Structure and Properties. J. Am. Chem. Soc. 117, 9515-9522.
Chehade, K. A., Andres, D. A., Morimoto, H., and Spielmann, H. P. (2000) design and synthesis of a transferable farnesyl pyrophosphate analogue to Ras by protein farnesyltransferase. J. Org. Chem. 65, 3027-33.
Chehade, K. A., Kiegiel, K., Isaacs, R. J., Pickett, J. S., Bowers, K. E., Fierke, C. A., Andres, D. A., and Spielmann, H. P. (2002) Photoaffinity analogues of farnesyl pyrophosphate transferable by protein farnesyl transferase. J. Am. Chem. Soc. 124, 8206-19.
Chehade, K. A. H., Andres, D. A., Morimoto, H., and Spielmann, H. P. (2000) Design and Synthesis of a Transferable Farnesyl Pyrophosphate. J. Org. Chem. 65, 3207-3033.
Crick, D. C., et al., (1998) Geranyl geraniol overcomes the block of cell proliferation by lovastatin in C6 glioma cells. J. Med. Chem. 38(8), 1372-9.
Crick, D. C., Andres, D. A., and Waechter, C. J. (1997) Novel salvage pathway utilizing farnesol and geranylgeraniol for protein isoprenylation. Biochem. Biophys. Res. Commun. 237, 483-7.
Crick, D. C., Andres, D. A., and Waechter, C. J. (1995) Farnesol is utilized for protein isoprenylation and the biosynthesis of cholesterol in mammalian cells. Biochem. Biophys. Res. Commun. 211, 590-9.
Danesi, R., McLellan, C. A., and Myers, C. E., (1995) Specific Labeling of Isoprenylated Proteins: Application to Study Inhibitors of the Post-Translational Farnesylation and Geranylgeraniolation. Biochm. Biophys. Res. Comm., 206(2), 637-43.
Dechat, Thomas, Takeshi Shimi, Stephen A. Adam, Antonio E. Rusinol, Douglas A. Andres, H. Peter Spielmann, Michael S. Sinensky, and Robert D. Goldman, (2007) Alterations in Mitosis and Cell Cycle Progression Caused by a Mutant Lamin A Known to Accelerate Human Aging. PNAS 104, 12, 4455-4960.
Dursina, B., et al., (2006) Identification and specificity profiling of protein prenyltransferase inhibitors using new fluorescent phosphoisoprenoids. J. Am. Chem. Soc. 128(9), 2822-35.
Eummer, J. T., et al. (1999) Novel Limonene Phosphate and Farnesyl Diphosphate Analogues: Design, Synthesis, and Evaluation as Potential Protein-Farnesyl Transferase Inhibitors. Biorg. and Med Chem., 7, 241-50.
Gibbs, B. S., Zahn, T. J., Mu, Y., Sebolt-Leopold, J. S., and Gibbs, R. A. (1999) Novel Farnesol and Geranylgeraniol Analogues: A Potential New Class of Anticancer Agents Directed against Protein Prenylation. J. Med. Chem. 42, 3800-3808.
Holstein, S. A., Wohlford-Lenane, C. L., Wiemer, D. F., and Hohl, R. J. (2003) Isoprenoid Pyrophosphate Analogues Regulate Expression of Ras-Related Proteins. Biochemistry 42, 4384-4391.
Kho, Y., Kim, S. C., Jiang, C., Barma, D., Kwon, S. W., Cheng, J., Jaunbergs, J., Weinbaum, C., Tamanoi, F., Falck, J., and Zhao, Y. (2004) A tagging-via-substrate technology for detection and proteomics of farnesylated proteins. Proc. Natl. Acad. Sci. U.S.A. 101, 12479-84.
Kim, K.W., et al., (2001) Inactivation of farnesyltransferase and geranylgeranyl-transferase I by caspase-3: cleavage of the common alpha subunit during apoptosis. Oncogene. 20(3), 358-66.
Lin, H. P., Hsu, S. C., Wu, J. C., Sheen, I. J., Yan, B. S., and Syu, W. J. (1999) Localization of isoprenylated antigen of hepatitis delta virus by anti-farnesyl antibodies. J. Gen. Virol. 80 (Pt 1), 91-6.
Liu, X. H., Suh, D. Y., Call, J., and Prestwich, G. D. (2004) Antigenic prenylated peptide conjugates and polyclonal antibodies to detect protein prenylation. Bioconjugate Chem. 15, 270-7.
Quellhorst, G. J., C.M. Allen, and M. Wessling-Resnick, (2001) Modification of Rab5 with a photoactivatable analog of geranylgeranyl diphosphate. J Biol Chem. 276(44), 40727-40733.
Rowell, C. A., Kowalczyk, J. J., Lewis, M. D., and Garcia, A. M. (1997) Direct demostration of geranylgeranylation and farnesylation of Ki-Ras in vivo, J. Biol. Chem. 272, 14093-7.
Thai, L., Rush, J. S., Maul, J. E., Devarenne, T., Rodgers, D. L., Chappell, J., and Waechter, C. J. (1999) Farnesol is utilized for isoprenoid biosynthesis in plant cells via farnesyl pyrophosphate formed by successive monophosphorylation reactions. Proc. Natl. Acad. Sci. U.S.A. 96, 13080-5.
Troutman J. M., Chehade, K. A., Kiegiel, K., Andres, D.A., Speilmann, H. P. (2004) Synthesis of acyloxymethyl ester prodrugs of the transferable protein farnesyl transferase substrate farnesyl methylenediphosphonate. Bioorg Med chem. Lett. 14 (19), 4979-82.

* cited by examiner

*Primary Examiner*—Shafiqul Haq
(74) *Attorney, Agent, or Firm*—Stites & Harbison PLLC; Mandy Wilson Decker

(57) ABSTRACT

Unnatural substrates of prenylation enzymes and antibodies that recognize unique moieties of prenylated proteins, which unique moieties are transferred from the unnatural substrates are used for detecting and isolating prenylated proteins, and for screening for inhibitors of prenylation enzymes.

10 Claims, 20 Drawing Sheets

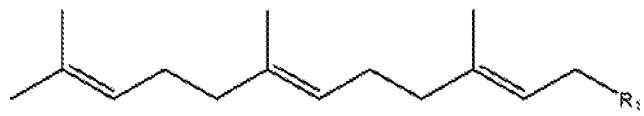

farnesyl alcohol (FOH): $R_1$ = OH
farnesyl diphosphate (FPP): $R_1$ = $P_2O_7^{3-}$
FIGURE 3A

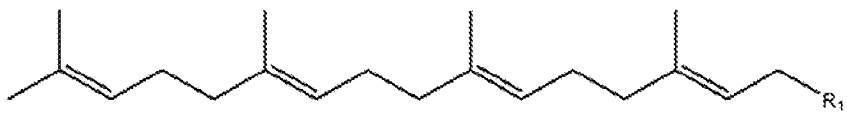

geranylgeraniol (GGOH): $R_1$ = OH
geranylgeraniol diphosphate (GGPP): $R_1$ = $P_2O_7^{3-}$
FIGURE 3B

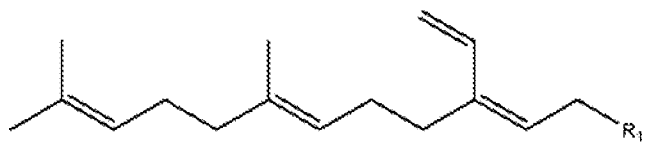

3-vinyl-farnesol: $R_1$ = OH
3-vinyl-farnesyl diphosphate (3vFPP): $R_1$ = $P_2O_7^{3-}$
FIGURE 3C

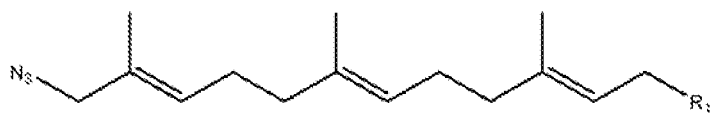

8-azido-farnesol: $R_1$ = OH
FIGURE 3D

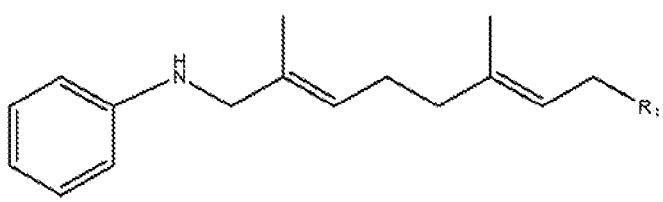

anilinogeraniol (AGOH): $R_1$ = OH
anilinogeranyl diphosphate (AGPP): $R_1$ = $P_2O_7^{3-}$
FIGURE 3E

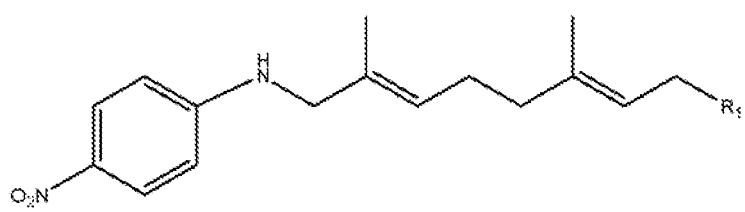

$p$NO$_2$-anilinogeraniol (NAGOH): $R_1$ = OH
$p$NO$_2$-anilinogeranyl diphosphate (NAGPP): $R_1$ = $P_2O_7^{3-}$
FIGURE 3F

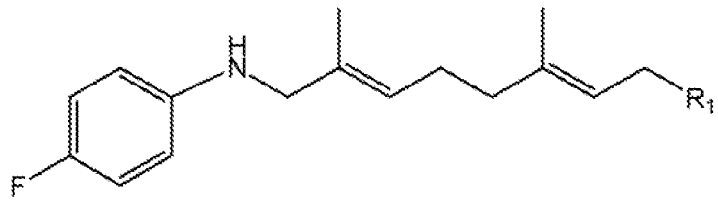

*p*-Fluoro-anilinogeraniol (pF-AGOH): $R_1$ = OH
*p*-Fluoro-anilinogeranyl diphosphate (pF-AGPP): $R_1 = P_2O_7^{3-}$
FIGURE 3G

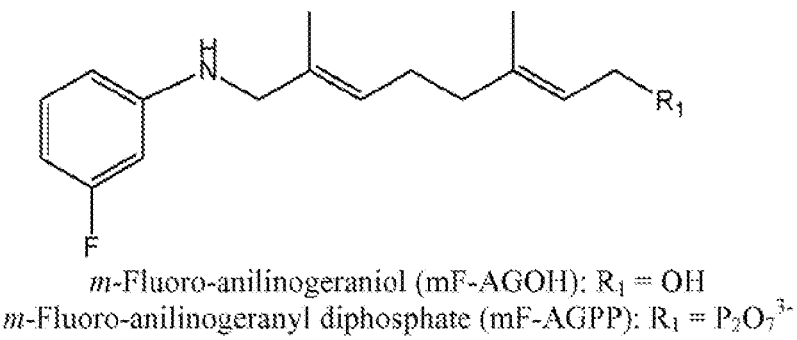

*m*-Fluoro-anilinogeraniol (mF-AGOH): $R_1$ = OH
*m*-Fluoro-anilinogeranyl diphosphate (mF-AGPP): $R_1 = P_2O_7^{3-}$
FIGURE 3H

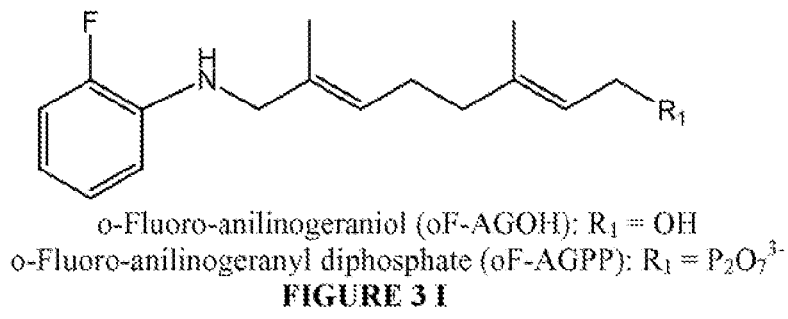

o-Fluoro-anilinogeraniol (oF-AGOH): $R_1$ = OH
o-Fluoro-anilinogeranyl diphosphate (oF-AGPP): $R_1 = P_2O_7^{3-}$
FIGURE 3 I

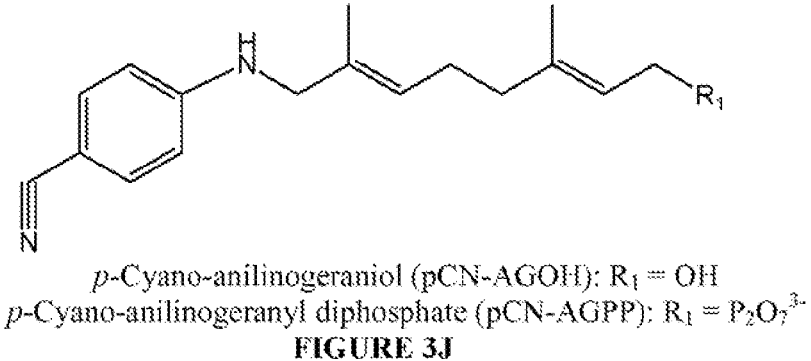

*p*-Cyano-anilinogeraniol (pCN-AGOH): $R_1$ = OH
*p*-Cyano-anilinogeranyl diphosphate (pCN-AGPP): $R_1 = P_2O_7^{3-}$
FIGURE 3J

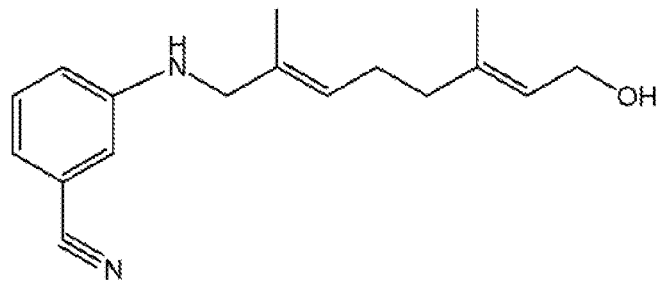

*m*-Cyano-anilinogeraniol (mCN-AGOH): $R_1$ = OH
*m*-Cyano-anilinogeranyl diphosphate (mCN-AGPP): $R_1$ = $P_2O_7^{3-}$
FIGURE 3K

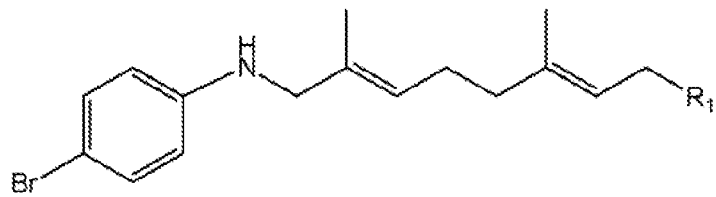

*p*-Bromo-anilinogeraniol (pBr-AGOH): $R_1$ = OH
*p*-Bromo-anilinogeranyl diphosphate (pBr-AGPP): $R_1$ = $P_2O_7^{3-}$
FIGURE 3L

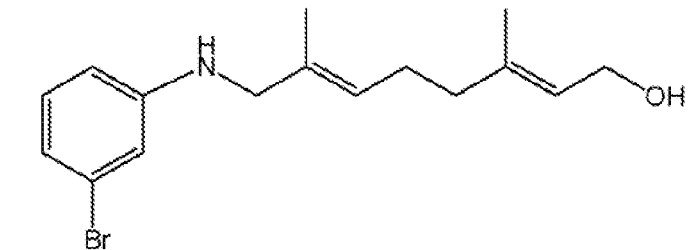

*m*-Bromo-anilinogeraniol (mBr-AGOH): $R_1$ = OH
*m*-Bromo-anilinogeranyl diphosphate (mBr-AGPP): $R_1$ = $P_2O_7^{3-}$
FIGURE 3M

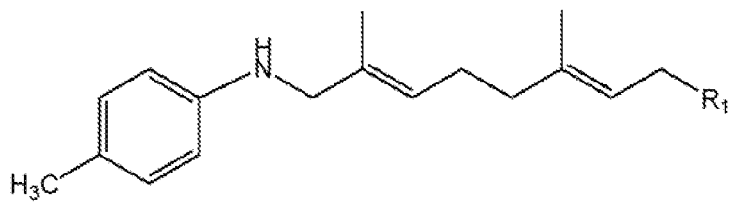

*p*-Methyl-anilinogeraniol (pMe-AGOH): $R_1$ = OH
*p*-Methyl-anilinogeranyl diphosphate (pMe-AGPP): $R_1$ = $P_2O_7^{3-}$
FIGURE 3N

*m*-Methyl-anilinogeraniol (mMe-AGOH): $R_1 = OH$
*m*-Methyl-anilinogeranyl diphosphate (mMe-AGPP): $R_1 = P_2O_7^{3-}$ anilinofarnesiol (AFOH): $R_1 = OH$
anilinofarnesyl diphosphate (AFPP): $R_1 = P_2O_7^{3-}$

*p*NO$_2$-anilinofarnesiol (AFOH): $R_1 = OH$
*p*NO$_2$-anilinofarnesyl diphosphate (AFPP): $R_1 = P_2O_7^{3-}$ C-terminal portion of modified RDJ2 Protein
$R_1$ = H
$R_1$ = farnesyl
$R_1$ = 8-anilinogeranyl
$R_1$ = pNO$_2$-anilinogeranyl C-terminal portion of modified H-RAS Protein
$R_1$ = H
$R_1$ = farnesyl
$R_1$ = 8-anilinogeranyl
$R_1$ = pNO$_2$-anilinogeranyl

ANTIBODIES AND UNNATURAL SUBSTRATES OF PRENYLATION ENZYMES FOR USE IN DETECTING AND ISOLATING PRENYLATED PROTEINS

CROSS REFERENCES TO RELATED APPLICATIONS

This application claims priority from U.S. Provisional Application Ser. No. 60/701,162 filed Jul. 21, 2005, the entire disclosure of which is incorporated herein by this reference.

STATEMENT REGARDING FEDERALLY SPONSORED RESEARCH

Research for this invention was made with support from the National Institute of Health Grant Number NIH R01 GM66152-01.

FIELD OF THE INVENTION

The present invention relates to detecting and isolating prenylated proteins, and screening for inhibitors of enzymes facilitating protein prenylation. More specifically, the present invention relates to newly identified antibodies to detect prenylated proteins and unnatural substrates of enzymes that catalyze protein prenylation reactions.

BACKGROUND OF TILE INVENTION

A wide variety of proteins require post-translational prenylation to participate normally in various cellular processes. For example, proteins such as Ras must become prenylated for proper membrane localization and activity. See e.g., Adjei, (2003) *Lung Cancer* 41 Suppl 1, S55-62; Rowinsky, et at. (1999) *J Clin Oncol* 17, 3631-52; Zhu, et al., and Sebti, S. M. (2003) *Curr Opin Investig Drugs* 4, 1428-35; Zhang, et al. (1996) Annu Rev Biochem 65, 241-69; Vergnes, et al. (2004) *Proc Natl Acad Sci U S A* 101, 10428-33.

Protein prenylation includes protein farnesylation, which involves the transfer of a farnesyl moiety to a protein and protein geranylgeranylation, which involves the transfer of a geranylgeranyl moiety to a protein. Farnesyl diphosphate (FPP) is the natural substrate of farnesyl transferase (FTase), which catalyzes the transfer of a farnesyl moiety from FPP to proteins. A group of compounds known as FTase inhibitors (FTIs) have the ability to block protein farnesylation. Similarly, geranylgeranyl diphosphate (GGPP) is the natural substrate of geranylgeranyl transferase I (GGTaseI), which catalyzes the transfer of a geranylgeranyl moiety from GGPP to proteins. A group of compounds known as GGTaseI inhibitors have the ability to block protein geranylgeranylation.

FTase catalyzes the farnesylation, and GGTaseI catalyzes the geranylgeranylation, of proteins with a cysteine residue located in a C-terminal $Ca_1Ca_2X$ motif, where C is the modified cysteine, $a_1$ and $a_2$ are often an aliphatic residue, and X is Ser, Met, Ala, or Gln. See Roskoski, R., Jr. (2003) *Biochem Biophys Res Commun* 303, 1-7; Dunten, et al. (1998) *Biochemistry* 37, 7907-7912; Caplin, et al. (1998) J Biol Chem 273, 9472-9.

As mentioned above, prenylation of proteins, such as Ras, is often required for proper participation of the protein in various cellular processes. Specifically, prenylation is obligatory for the oncogenic effects of mutant Ras. See Adjei, (2001) *J Natl Cancer Inst* 93,1062-74. Mutated forms of Ras genes are among the most common genetic abnormality in human cancer, occurring in 10 to 30% of all neoplasms. See Anwar, et al. (1992) *Cancer Res* 52, 5991-6; Watanabe, et al. (1994) *Int J Cancer* 58, 174-8; Konishi, et al. (1995) *Am J Pathol* 147, 1112-22; Konishi, et al. (1997) *Prostate* 30, 53-7. These observations have lead to the development of a number of FTIs, which block protein farnesylation, and GGTaseI Inibitors, which block geranylgeranylation. FTIs, for example, have the ability to inhibit Ras farnesylation, appropriate subcellular localization and activity, in addition to inhibiting growth of Ras-transformed cells. Various FTIs are being studied for their efficacy as antineoplastic agents. See Santucci, et al. (2003) *Cancer Control* 10, 384-7; Sebti, et al. (2000) *Oncogene* 19, 6584-93; Reid, T. S., and Beese, L. S. (2004) *Biochemistry* 43, 6877-84.

Prenylation is the first and obligatory step in a series of post-translational modifications which mediate membrane localization and possibly protein-protein interactions for a variety of proteins involved in cellular regulatory events. See Ramamurthy, et al. (2003) *Proc Natl Acad Sci U S A* 100, 12630-5; Scheffzek, et al. (2000) *Nat. Struc. Biol.* 7, 122-126; Chen, et al. (1999) *Chin Med Sci J* 14, 138-44. Subsequent to farnesylation, the $a_1a_2X$ peptide is cleaved by the endopeptidase RCE1 followed by carboxymethylation of the now terminal prenylated cysteine residue by the carboxymethyltransferase Icmt. See Bergo, et al. (2002) *Mol Cell Biol* 22, 171-81; Michaelson, et al (2005) *Mol Biol Cell*.

Similar post-translational modifications occur on the relatively small set of farnesylated cellular proteins, not all of which have been identified or characterized. Therefore, the rapid and selective detection of cellular protein prenylation status and easy isolation of farnesylated proteins would be helpful to understanding both the function of farnesylated proteins and of FTase inhibitors. Similar post-translational modifications also occur on a set of geranylgeranylated cellular proteins, and the rapid and selective detection of cellular protein prenylation status and easy isolation of geranylgeranylated proteins would be helpful to understanding both the function of geranylgeranylated proteins and of GGTaseI inhibitors.

Monitoring the prenylation status of proteins in cells is a challenging undertaking. Initially, prenylation of proteins was discovered by metabolic labeling with [$^3$H]mevalonolactone. See Maltese (1990) *Faseb J* 4, 3319-28. In these experiments, some of the tritium label was incorporated into both farnesylated and geranylgeranylated proteins. Subsequently, a salvage pathway was discovered where radiolabeled farnesol (FOH) and geranylgeraniol (GGOH), precursors of FPP and GGPP, were selectively incorporated into their respective farnesylated or geranylgeranylated proteins. See, e.g., Andres, et al. (1999) *Methods Mol Biol* 116, 107-23. A drawback of these approaches is the inherently low sensitivity of autoraidographic detection of the weak tritium β-emission. In fact, it can take up to four weeks to visualize proteins extracted from cells labeled with tritiated mevalonate or farnesol by audioradiography. See Gibbs, et al. (1999) *J. Med. Chem.* 42, 3800-3808. Also, the incorporation of tritiated prenyl groups does not provide a convenient method for isolation of these modified proteins.

The facile detection, isolation and purification of prenylated proteins based solely on their post-translational modification status is useful for developing an understanding of the mechanism of cellular growth inhibition by inhibitors of enzymes catalyzing prenylation reactions (e.g., FTIs, GGTaseI Inhibitors).

Antibodies are useful both in the routine detection and immunoprecipitation of proteins with other post-translational modifications, such as phosphorylation. See Gronborg, et al. (2002) *Mol Cell Proteomics* 1, 517-27. However, reports of previous attempts to produce antibodies to detect farnesylated proteins or geranylgeranylated proteins have not had overwhelming success. For example, two of these reports described non-specific antibodies that could not differentiate between proteins modified by farnesylation, geranylgeranylation or other lipids. See Liu, et al. (2004) *Bioconjug Chem* 15, 270-7; Lin, et al. (1999) *J Gen Virol* 80 (*Pt* 1), 91-6. The other report from Baron et al. does describe the production of anti-farnesyl antibodies specific for farnesylation, but the analysis for specificity was limited. Baron, et al. (2000) *Proc Natl Acad Sci U S A* 97, 11626-31. All of the commercially available sources for anti-farnesyl antibodies cross-react with geranylgeranylated proteins.

Several unnatural analogs of FPP appear to be utilized by cells and incorporated into the proteins by FTase, including the unnatural FPP analogue 3-vinyl-farenesol, a pro-drug of the FTase transferable 3-vinyl-farnesyl diphosphate (3vFPP), and 8-azido-farnesol. A tagging-via-substrate (TAS) approach to the detection and isolation of farnesylated proteins involving the incorporation of 8-azido-farnesol into cellular proteins has been developed by Kho, et al. (2004) *Proc Natl Acad Sci U S A* 101, 12479-84. By this approach, modified proteins are isolated from cell lysates using a biotinylated phosphine capture reagent and subsequently identified by mass spectrometry. However, the sensitivity is relatively low and the technique does not lend itself to the routine detection of modified proteins.

Accordingly, there remains a need in the art for a method and system for convenient, rapid, and selective detection, identification, and isolation of prenylated proteins, including farnesylated proteins and geranylgeranylated proteins, which satisfactorily address the above-identified problems.

SUMMARY OF THE INVENTION

The present invention overcomes the difficulties associated with known methods of detecting and isolating prenylated proteins by providing unnatural substrates of prenylation enzymes and antibodies recognizing uniquie moieties of prenylated proteins, which unnatural substrates and antibodies may be used to detect and isolatE prenylated proteins. In this regard, the present invention also includes methods and systems for detecting and/or isolating prenylated proteins using the unnatural substrates and antibodies of the present invention. The present invention further includes methods and systems for screening for prenylation enzyme inhibitors using the unnatural substrates and antibodies of the present invention.

DESCRIPTION OF EMBODIMENTS OF THE INVENTION

As used in the present specification, the following words and phrases are generally intended to have the meanings as set forth below, except to the extent that the context in which they are used indicates otherwise A "prenylation enzyme" is an enzyme that catalyzes a protein prenylation reaction. Examples of prenylation enzymes include: farnesyl transferase (FTase), and geranylgeranyl transferase I (GGTaseI).

An "unnatural substrate" is a compound that acts as a substrate of a prenylation enzyme, but is not a natural substrate of the prenylation enzyme.

A "precursor to an unnatural substrate" is a compound that can be metabolized into an unnatural substrate of a prenylation enzyme.

Figure 3:
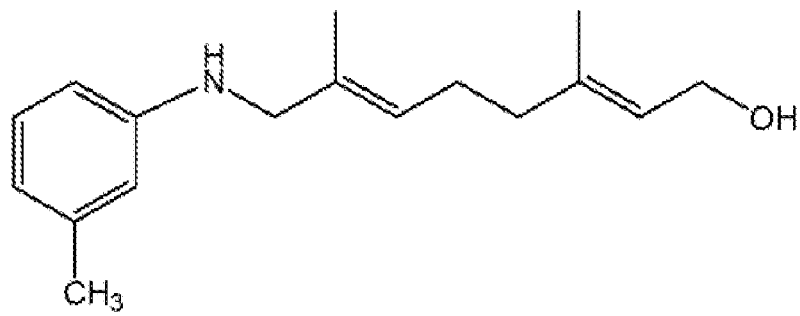
FIGS. 3A through 3Q are chemical formulas of natural and unnatural substrates of prenylation enzymes, and chemical formulas of the precursors of the natural and unnatural substrates.
Figure 3P:
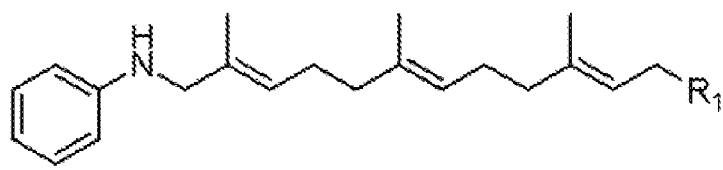
Figure 3Q:
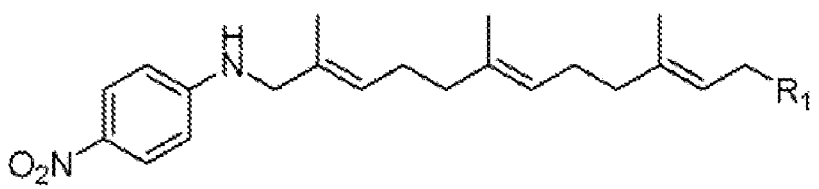

"protein prenylation" is a process by which a protein is modified with a moiety from a natural substrate or an unnatural substrate of a prenylation enzyme. A "prenylated protein" is a protein that has been modified with a moiety from a natural substrate or an unnatural substrate of a prenylation enzyme. With reference to FIGS. 3A-3Q, examples of such moieties include, but are not limited to: farnesyl (F) moiety; geranylgeranyl (GG) moiety; anilinogeranyl (AG) moiety; para-nitro-anilinogeranyl (pNO$_2$-anilinogeranyl, NAG) moiety; para-fluoro-anilinogeraniol (pF-AG) moiety; meta-fluoro-anilinogeranyl (mF-AG) moiety; ortho-fluoro-anilinogeranyl (oF-AG) moiety; para-cyano-anilinogeranyl (pCN-AG) moiety; meta-cyano-anilinogeranyl (mCN-AG) moiety; para-bromo-anilinogeranyl (pBR-AG) moiety; meta-bromo-anilinogeranyl (mBr-AG) moiety; para-methyl-anilioingeranyl (pMe-AG) moiety; meta-methyl-anilinogeranyl (mMe-AG) moiety; anilinofarnesyl (AF) moiety; and para-nitro-anilinofarnesyl (pNO$_2$-anilinofarnesyl, NAF) moiety.

A "unique moiety" is a moiety of an unnatural substrate of a prenylation enzyme, which unique moiety can be transferred to a protein during a prenylation reaction using a prenylation enzyme. Examples of such unique moieties include, but are not limited to: anilinogeranyl (AG) moiety; para-nitro-anilinogeranyl (pNO$_2$-anilinogeranyl, NAG) moiety; para-fluoro-anilinogeraniol (pF-AG) moiety; meta-fluoro-anilinogeranyl (mF-AG) moiety; ortho-fluoro-anilinogeranyl (oF-AG) moiety; para-cyano-anilinogeranyl (pCN-AG) moiety; meta-cyano-anilinogeranyl (mCN-AG) moiety; para-bromo-anilinogeranyl (pBR-AG) moiety; meta-bromo-anilinogeranyl (mBr-AG) moiety; para-methyl-anilinogeranyl (pMe-AG) moiety; meta-methyl-anilinogeranyl (mMe-AG) moiety; anilinofarnesyl (AF) moiety; and para-nitro-anilinofarnesyl (pNO$_2$-anilinofarnesyl, NAF) moiety.

The present invention includes: unnatural substrates of prenylation enzymes; isolated antibodies that recognize unique moieties of prenylated proteins; methods and systems for detecting and/or isolating prenylated proteins using the isolated antibodies and unnatural substrates; and methods and systems for screening for inhibitors of prenylation enzymes using the isolated antibodies and unnatural substrates.

Figure 1:
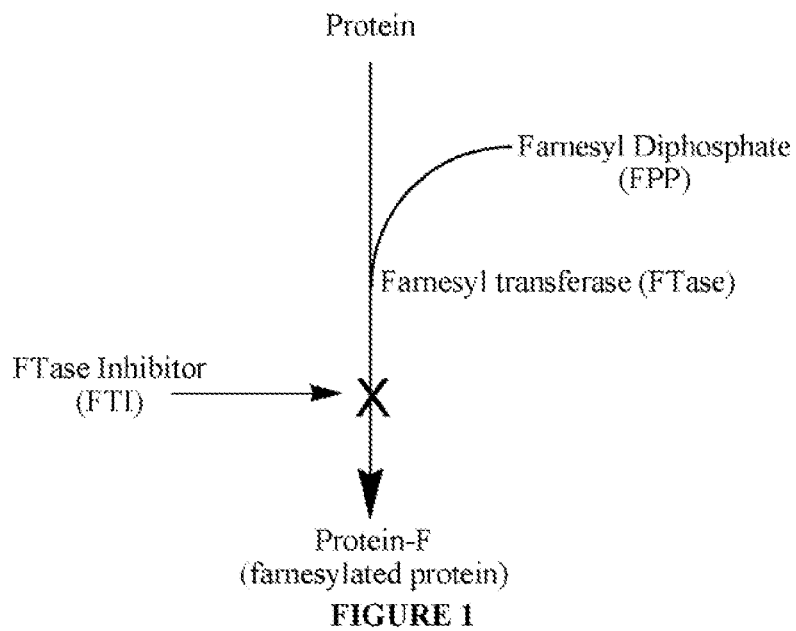
FIG. 1 is an illustration of a protein farnesylation reaction, wherein farnesyl transferase (FTase) catalyzes the transfer of a farnesyl moiety from farnesyl diphosphate (FPP), the natural substrate of FTase, to a protein.
Figure 2:
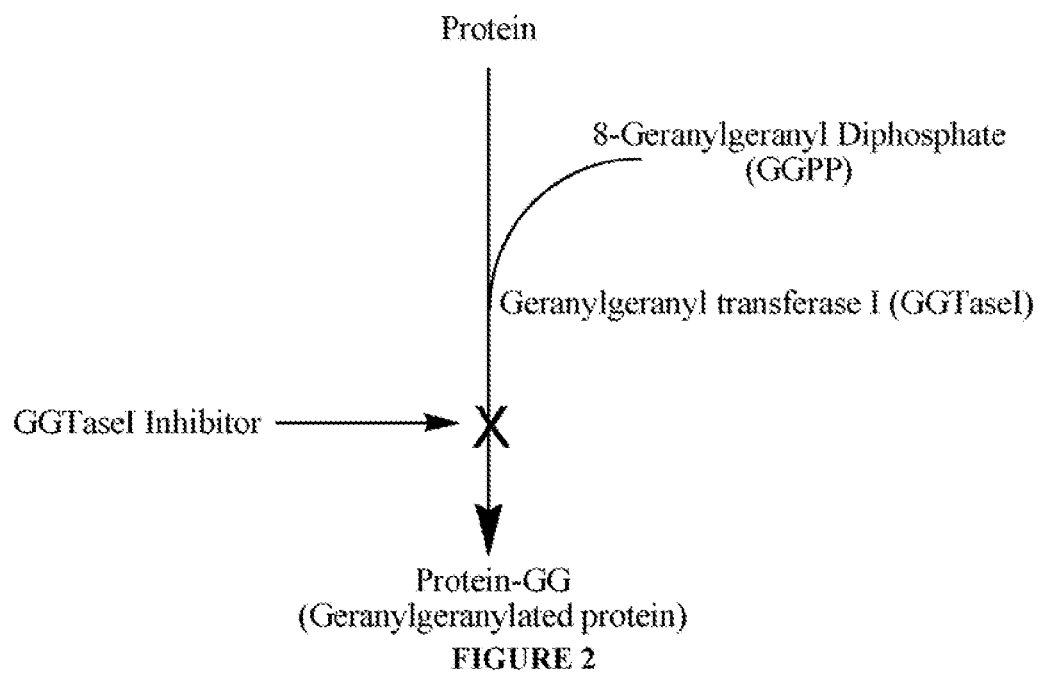
FIG. 2 is an illustration of a protein geranylgeranylation reaction, wherein geranylgeranyl transferase I (GGTaseI) catalyzes the transfer of a geranylgeranyl moiety from geranylgeranyl diphosphate (GGPP), the natural substrate of GGTaseI, to a protein.

As mentioned above with reference to FIG. 1, farnesyl diphosphate (FPP) is the natural substrate of farnesyl transferase (FTase), which catalyzes the transfer of a farnesyl moiety from FPP to proteins. As also mentioned above with reference to FIG. 2, geranylgeranyl diphosphate (GGPP) is the natural substrate of geranylgeranyl transferase I (GGTaseI), which catalyzes the transfer of a geranylgeranyl moiety from GGPP to proteins. Such prenylation reactions, and the prenylated proteins that are produced thereby, are difficult to study because of the sensitivity, convenience, speed, selectivity and specificity issues associated with known methods for detecting and isolating prenylated proteins.

Accordingly, the present invention includes unnatural substrates of prenylation enzymes and isolated antibodies, which may be used to practice methods of the present invention for detecting and isolating prenylated proteins without the difficulties associated with known methods. Such methods of the present invention will be described in more detail below.

With reference to FIGS. 3E through 3Q, exemplary unnatural substrates of the present reaction include: anilinogeranyl diphosphate (AGPP); para-nitro-anilinogeranyl diphosphate (pNO$_2$-anilinogeranyl diphosphate, NAGPP); para-fluoro-anilinogeraniol diphosphate (pF-AGPP); meta-fluoro-anilinogeranyl diphosphate (mF-AGPP); ortho-fluoro-anilinogeranyl diphosphate (oF-AGPP); para-cyano-anilinogeranyl diphosphate (pCN-AGPP); meta-cyano-anilinogeranyl diphosphate (mCN-AGPP); para-bromo-anilinogeranyl diphosphate (pBR-AGPP); meta-bromo-anilinogeranyl diphosphate (mBr-AGPP); para-methyl-anilinogeranyl diphosphate (pMe-AGPP); meta-methyl-anilinogeranyl diphosphate (mMe-AGPP); anilinofarnesyl diphosphate (AFPP); and para-nitro-anilinogeranyl diphosphate (pNO$_2$-anilinofarnesyl, NAFPP). Other unnatural substrates that may be used in accordance with the present invention also include: anilinogeranyl diphosphates and anilinogeranyl diphosphates with small substitutions (e.g., nitro, methyl, bromo, fluoro, cyano, chloro, and the like) in the aniline ring, and other unnatural substrates of prenylation enzymes, such as those set forth in U.S. Pat. No. 6,284,910, which is incorporated herein by reference.

The isolated antibodies of the present invention recognize unique moieties of prenylated proteins, which unique moieties are transferred from the unnatural substrates to the proteins in prenylation reactions. Exemplary antibodies of the present invention include: an isolated antibody that recognizes proteins modified with an anilinogeranyl moiety (Anti-AG), an isolated antibody that recognizes proteins modified with a $pNO_2$-anilinogeranyl moiety (Anti-NAG), and an isolated antibody that recognizes proteins modified with an anilinogeranyl moiety and proteins modified with an anilinofarnesyl moiety (mAG). An exemplary manner of generating the antibodies, identified herein as Anti-AG, Anti-NAG, and mAG, is described below in the Examples.

Turning now to FIGS. 4A through 5B, the participation of exemplary unnatural substrates of prenylation enzymes in prenylation reactions will now be described. The described prenylation reactions set forth in FIGS. 4A through 5B are merely exemplary and many other prenylation reactions using various unnatural substrates of prenylation enzymes are possible and various isolated antibodies can be used to recognize the unique moieties of the resulting prenylated proteins, which variations are contemplated by the present invention.

Figure 4A:
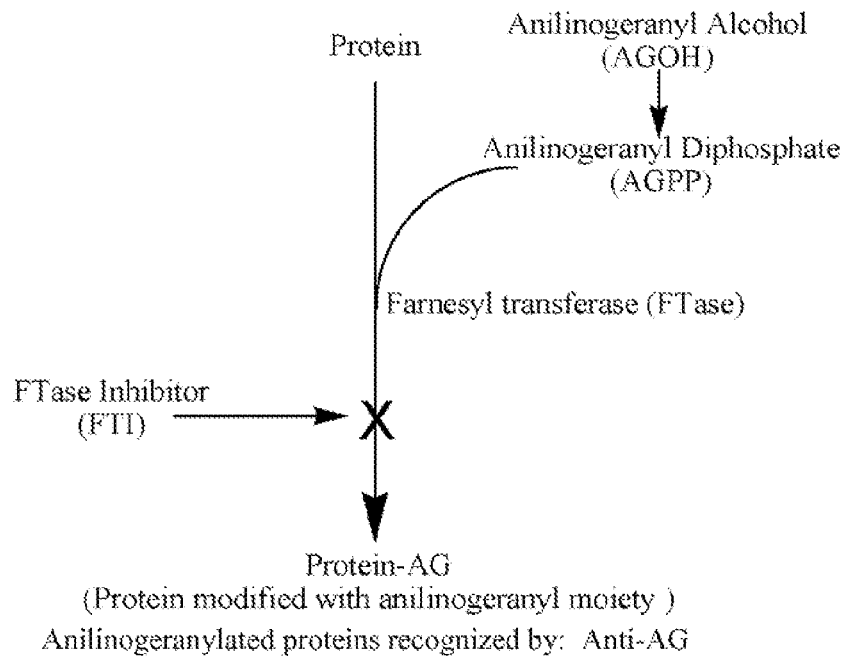
FIG. 4A is an illustration of a protein farnesylation reaction, wherein farnesyl transferase (FTase) catalyzes the transfer of an anilinogeranyl moiety from anilinogeranyl diphosphate (AGPP), an unnatural substrate of FTase, to a protein.

With reference to FIG. 4A, anilinogeranyl diphosphate (AGPP) is an unnatural substrate of farnesyl transferase (FTase). As such, FTase can catalyze the transfer of the unique anilinogeranyl (AG) moiety from AGPP to a protein that is capable of being farnesylated; and FTase Inhibitors (FTIs) have the ability to block the transfer of the unique AG moiety from AGPP to the protein. Anilinogeranyl alcohol (AGOH) is a precursor to the unnatural substrate, AGPP. AGOH can be metabolized into AGPP in order to participate in the prenylation reaction. The prenylated protein bearing the unique AG moiety can be recognized by the Anti-AG antibody.

Figure 4B:
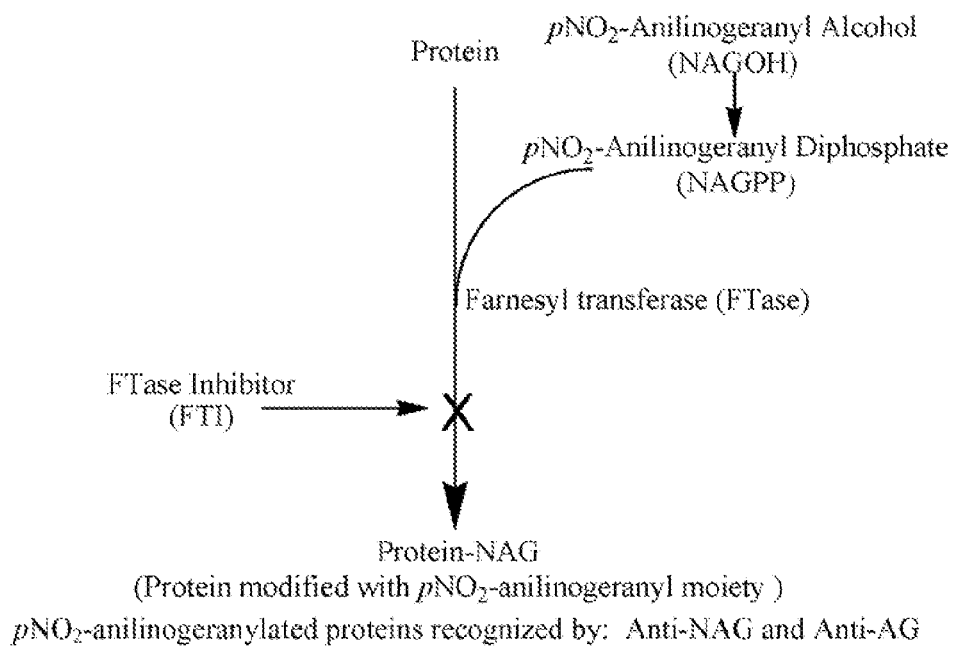
FIG. 4B is an illustration of a protein farnesylation reaction, wherein farnesyl transferase (FTase) catalyzes the transfer of a pNO$_2$-anilinogeranyl moiety from pNO$_2$-anilinogeranyl diphosphate (NAGPP), an unnatural substrate of FTase, to a protein.

With reference to FIG. 4B, $pNO_2$-anilinogeranyl diphosphate (NAGPP) is another unnatural substrate of FTase. As such, FTase can catalyze the transfer of the unique $pNO_2$-anilinogeranyl (NAG) moiety from NAGPP to a protein that is capable of being farnesylated; and FTIs have the ability to block the transfer of the unique NAG moiety from NAGPP to the protein. $pNO_2$-anilinogeranyl alcohol (NAGOH) is a precursor to the unnatural substrate, NAGPP. NAGOH can be metabolized into NAGPP in order to participate in the prenylation reaction. The prenylated protein bearing the unique NAG moiety can be recognized by the Anti-AG antibody and the Anti-NAG antibody.

Figure 5A:
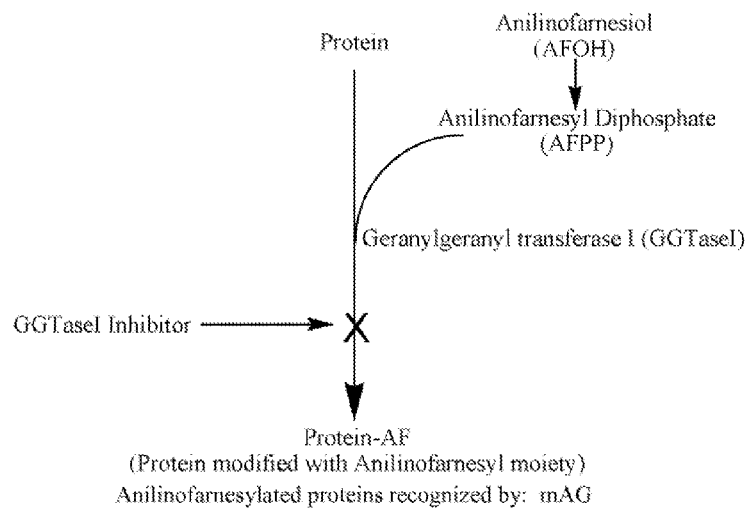
FIG. 5A is an illustration of a protein geranylgeranylation reaction, wherein geranylgeranyl transferase I (GGTaseI) catalyzes the transfer of an anilinofarnesyl moiety from anilinofarnesyl diphosphate (AFPP), an unnatural substrate of GGTaseI, to a protein.

With reference to FIG. 5A, anilinofarnesyl diphosphate (AFPP) is an unnatural substrate of geranylgeranyl transferase I (GGTaseI). As such, GGTaseI can catalyze the transfer of the unique anilinofarnesyl (AF) moiety from AFPP to a protein that is capable of being geranylgeranylated; and GGTaseI Inhibitors have the ability to block the transfer of the unique AF moiety from AFPP to the protein. Anilinofarnesiol (AFOH) is a precursor to the unnatural substrate, AFPP. AFOH can be metabolized into AFPP in order to participate in the prenylation reaction. The prenylated protein bearing the unique AF moiety can be recognized by the mAG antibody.

Figure 5B:
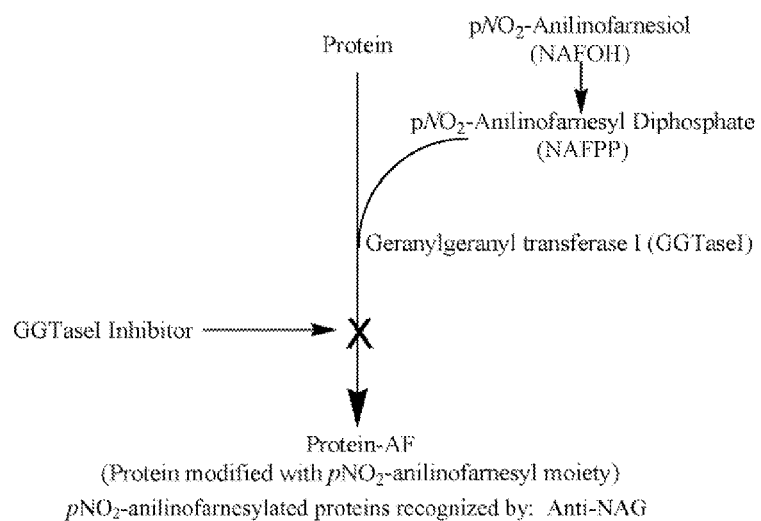
FIG. 5B is an illustration of a protein geranylgeranylation reaction, wherein geranylgeranyl transferase I (GGTaseI) catalyzes the transfer of a pNO$_2$-anilinofarnesyl moiety from pNO$_2$-anilinofarnesyl diphosphate (NAFPP), an unnatural substrate of GGTaseI, to a protein.

With reference to FIG. 5B, $pNO_2$-anilinofarnesyl diphosphate (NAFPP) is another unnatural substrate of GGTaseI. As such, GGTaseI can catalyze the transfer of the unique $pNO_2$-anilinofarnesyl (NAF) moiety from NAFPP to a protein that is capable of being geranylgeranylated; and GGTaseI Inhibitors have the ability to block the transfer of the unique NAF moiety from NAFPP to the protein. Para-$NO_2$-anilinofarnesiol (NAFOH) is a precursor to the unnatural substrate, NAFPP. NAFOH can be metabolized into NAFPP in order to participate in the prenylation reaction. The prenylated protein bearing the unique NAF moiety can be recognized by the Anti-NAG antibody.

The above mentioned unnatural substrates and other exemplary unnatural substrates are set forth below in Table 1, which identifies each unnatural substrates as part of a group including: a prenylation enzyme, an unnatural substrate of the prenylation enzyme, a precursor to the unnatural substrate, a unique moiety of the unnatural substrate, and at least one antibody that recognizes the unique moiety.

TABLE 1

| | Prenylation Enzyme | Unnatural Substrate | Precursor | Unique Moiety | Antibody(ies) |
|---|---|---|---|---|---|
| Group 1 | FTase | AGPP | AGOH | AG | Anti-AG |
| Group 2 | FTase | NAGPP | NAGOH | NAG | Anti-AG Anti-NAG |
| Group 3 | FTase | Para-fluoro-AGPP | Para-fluoro AGOH | Para-fluoro-AG | Anti-AG |
| Group 4 | FTase | Meta-fluoro-AGPP | Meta-fluoro-AGOH | Meta-fluoro-AG | Anti-AG |
| Group 5 | FTase | Ortho-fluoro-AGPP | Ortho-fluoro-AGOH | Ortho-fluoro-AG | Anti-AG |
| Group 6 | FTase | Para-methyl-AGPP | Para-methyl-AGOH | Para-methyl-AG | Anti-AG |
| Group 7 | FTase | Meta-methyl-AGPP | Meta-methyl-AGOH | Meta-methyl-AG | Anti-AG |
| Group 8 | FTase | Meta-cyano-AGPP | Meta-cyano-AGOH | Meta-cyano-AG | Anti-AG Anti-NAG |
| Group 9 | FTase | Para-bromo-AGPP | Para-bromo-AGOH | Para-bromo-AG | Anti-AG Anti-NAG |
| Group 10 | FTase | Meta-bromo-AGPP | Meta-bromo-AGOH | Meta-bromo-AG | Anti-AG |
| Group 11 | FTase | Ortho-fluoro-AGPP | Ortho-fluoro-AGOH | Ortho-fluoro-AG | Anti-NAG |
| Group 11 | FTase | Para-cyano-AGPP | Para-cyano-AGOH | Para-cyano-AG | Anti-NAG |
| Group 12 | GGTaseI | AFPP | AFOH | AF | mAG |
| Group 13 | GGTaseI | NAFPP | NAFOH | NAF | Anti-NAG |

The present invention includes systems and methods for detecting or isolating prenylated proteins using the unnatural substrates and the antibodies of the present invention. An exemplary system made in accordance with the present invention includes a prenylation reaction group having: a prenylation enzyme; an unnatural substrate to the prenylation enzyme having a unique moiety, or a precursor to the unnatural substrate; and an antibody that recognizes the unique moiety. A sample containing at least one protein can be allowed to interact with the prenylation enzyme, and the unnatural substrate or precursor thereto. Resulting prenylated proteins can be detected using the antibody by immunodetection methods known to those skilled in the art. Alternatively or additionally, resulting prenylated proteins can be isolated using the antibody by immunoprecipitation methods known to those skilled in the art.

Figure 6:
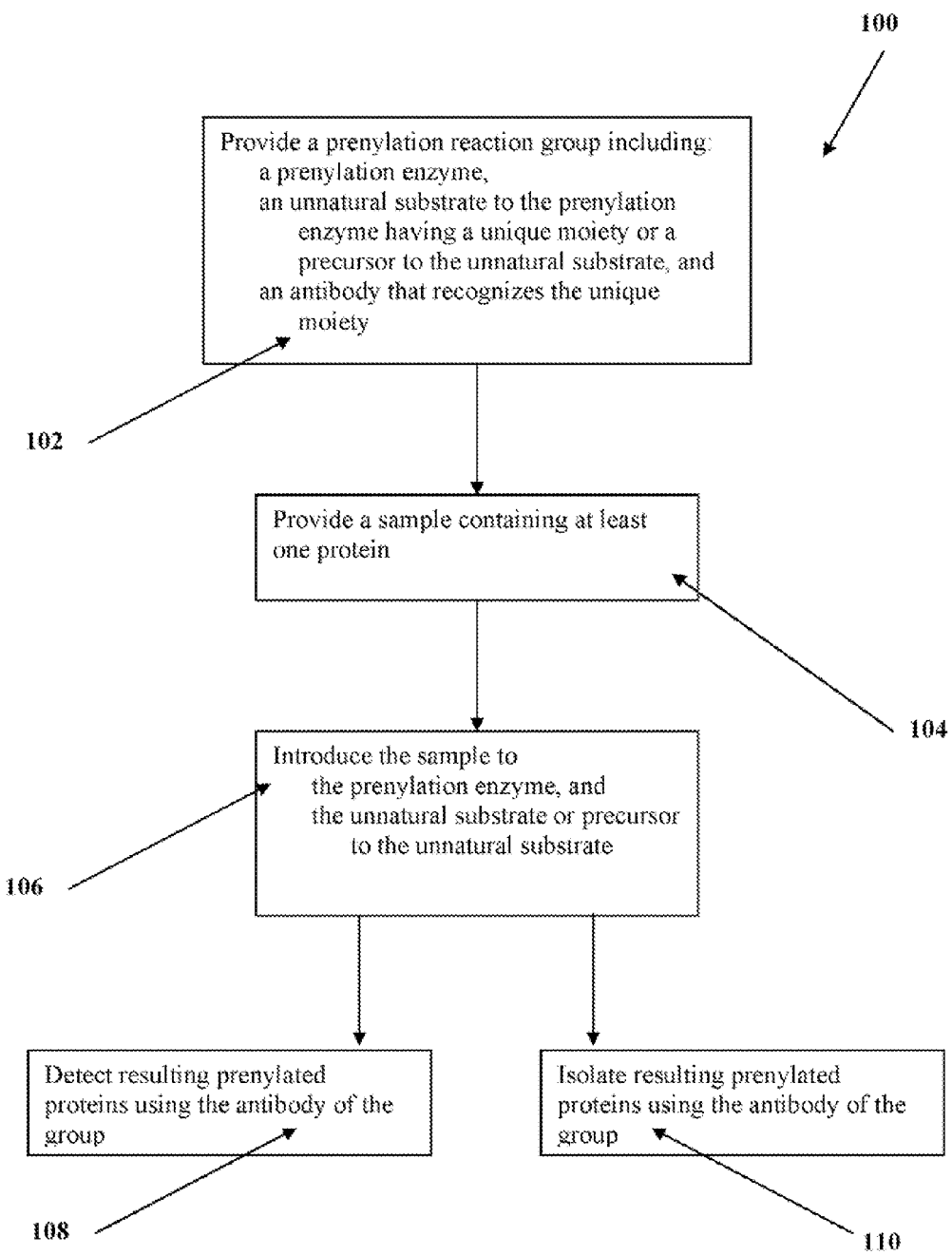
FIG. 6 is a flow chart illustrating the steps involved in an exemplary method for detecting and/or isolating prenylated proteins.

With reference to FIG. 6, an exemplary method 100 for detecting or isolating prenylated proteins includes: providing a prenylation reaction group including a prenylation enzyme, an unnatural substrate to the prenylation enzyme having a unique moiety or a precursor to the unnatural substrate, and an antibody that recognizes the unique moiety 102; providing a sample containing at least one protein 104; introducing the sample to the prenylation enzyme, and the unnatural substrate or precursor thereto 106; and detecting the resulting prenylated proteins using the antibody 108 or isolating the resulting prenylated proteins using the antibody 110.

With regard to the step in the exemplary method of providing a prenylation reaction group 102 various prenylation reaction groups containing different prenylation enzymes, unnatural substrates for precursors), and antibodies may be provided without departing from the spirit and scope of the present invention, so long as the selected unnatural substrate is an unnatural substrate of the selected prenylation enzyme, and selected unnatural substrate has a unique moiety that is recognized by the selected anibody. For example, components of the prenylation reaction group may be selected from a Group identified in Table 1, such as Group 1, wherein the prenylation enzyme is FTase, the unnatural substrate is AGPP, and the antibody is Anti-AG. For another example, components of the prenylation reaction croup may be selected from group 13 of Table 1, wherein the prenylation enzyme is GGTaseI, the unnatural substrate is NAFPP, and the antibody is Anti-NAG. Components taken from any discrete group of Table 1 are components of the prenylation reaction group that can be used in the exemplary method.

With regard to the step in the exemplary method of providing a sample containing at least one protein 104, various types of samples may be provided without departing from the spirit and scope of the present invention. For example, a sample containing simply a protein of interest may be provided, and the prenylation reaction may be conducted in vitro. When the method is conducted in vitro, it is often preferred that the unnatural substrate be selected for the prenylation reaction group, rather than the precursor to the unnatural substrate, because the sample may not contain the components necessary to metabolize the precursor into the unnatural substrate. For another example of a sample that may be provided, a sample of cells in culture may be provided and the prenylation reaction may be conducted in the cultured cell sample. The cells may be any type of cells capable of being grown in culture. For another example, a biological sample may be provided, such as a blood or serum sample, and the prenylation reaction may be conducted using the protein-containing sample of blood. The blood may be obtained from an animal of interest. The animal of interest may be, for example, an animal used for experimental purposes (e.g., mouse, rabbit, etc.), or a human patient. For another example, the sample may be provided as a whole animal of interest. The animal of interest could be involved in a particular treatment program and the exemplary method could be used to monitor the effects of the treatment program on protein prenylation status. For example, a patient of interest may be involved in a treatment program that involves administration of statins, and the method could be used to monitor the effects of the administered statins on protein prenylation status and the prenylated proteins may be isolated and studied.

With regard to the step in the exemplary method of introducing the sample to the prenylation enzyme, and the unnatural substrate or precursor 106, the type of sample that is provided will effect the manner in which the sample is allowed to interact with the prenylation enzyme, and the unnatural substrate or precursor. For example, if the sample simply contains a protein of interest, the sample, the prenylation enzyme, and the unnatural substrate may be combined in an appropriate reaction vessel held under appropriate conditions (e.g., conditions facilitating interaction of the sample with the prenylation enzyme and the unnatural substrate). For another example, if the sample includes cells in culture, the prenylation enzyme and the unnatural substrate (or precursor) may be added to growth medium surrounding the cells. For another example, if the sample is provided as a whole animal of interest, the prenylation enzyme and the unnatural substrate (or precursor) may be administered to the animal of interest by appropriate methods (e.g., administered orally, intravenously, etc.)

With regard to the step in the exemplary method of detecting prenylated proteins 108, the detection may be conducted using any immunodetection method known by those skilled in the art. With regard to the step in the exemplary method of isolating prenylated proteins 110, the isolation may be conducted using any immunoisolation method known by those skilled in the art. In certain cases, it may be desirable to isolate one or more proteins from the sample before exposing them to the antibody for immunodetection or immunoisolation. For example, if the sample is a sample of cells in culture, the cellular proteins may be extracted from the cells, using methods known in the art, before they are exposed to the antibody for immunodetection or immunoisolation. For another example, if the sample is provided as a whole animal of interest, a protein sample (e.g., urine, blood, tissue extraction) may be taken from the animal of interest and used for detecting or isolating prenylated proteins.

Additional samples may be provided, which additional samples can be examined concurrently with and compared to the first sample. For example, a first sample may be provided with a first protein of interest and a second sample may be provided with a second protein of interest. The first and second samples can be allowed to interact with the same prenylation enzyme and unnatural substrate. The detection of prenylated proteins in the first sample can be compared to the detection of prenylated proteins in the second sample to identify differences therebetween. Further samples may be provided, for example, as controls, which controls can be examined concurrently with other samples. Controls could include, for example, a sample that is allowed to interact with the prenylation enzyme, but not with the unnatural substrate or precursor. Of course, various modifications to the exemplary method are contemplated and will become apparent to those skilled in the art from consideration of the present specification.

The present invention includes systems and methods for screening for inhibitors of prenylation enzymes using the unnatural substrates and the antibodies of the present invention. An exemplary system made in accordance with the present invention includes a protein capable of being prenylated; and a prenylation reaction group having: a prenylation enzyme; an unnatural substrate to the prenylation enzyme having a unique moiety, or a precursor to the unnatural substrate; and an antibody that recognizes the unique moiety. A candidate prenylation enzyme inhibitor is screened by allowing the protein, the prenylation enzyme, and the unnatural substrate or precursor to interact with the candidate inhibitor. Resulting prenylated proteins are detected. The candidate inhibitor is identified as an actually inhibitor when the detected presence of prenylated proteins is below a predetermined level.

The predetermined level may be identified, for example, by quantifying the detected prenylated proteins using methods known to those skilled in the art and comparing the quantified prenylated protein levels to a standard curve plotting levels of prenylated proteins as a function of enzyme inhibition. For another example, the predetermined level may be identified using a control sample that does not contain the candidate inhibitor. In this regard, when a control sample that does not contain the candidate inhibitor is examined concurrently with a test sample that contains the candidate inhibitor, the candidate inhibitor is identified as an actual inhibitor when the detected presence of prenylated proteins in the test sample is less than the detected presence of prenylated proteins in the control sample.

Figure 7A:
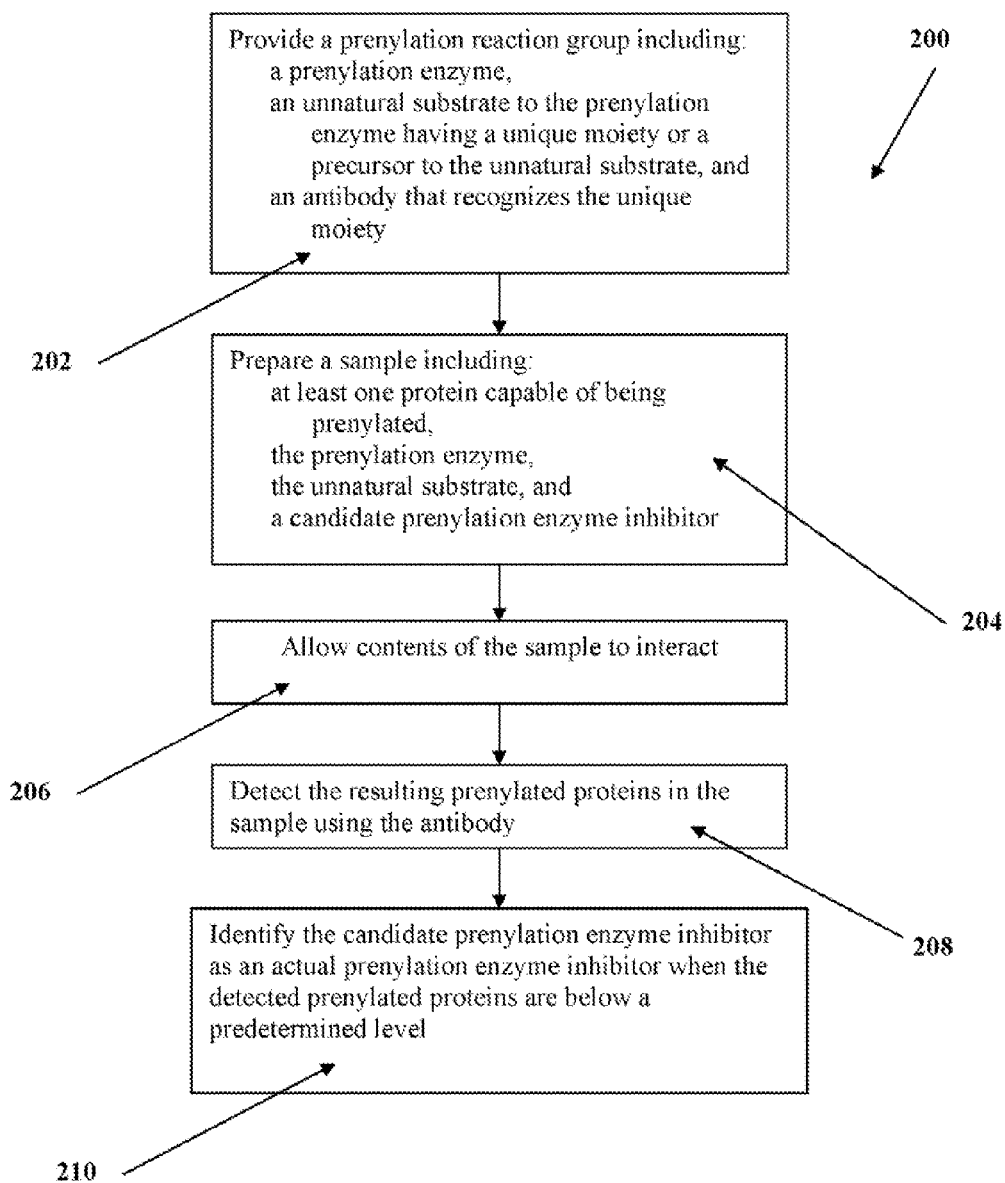
FIG. 7A is a flow chart illustrating the steps involved in an exemplary method for screening for inhibitors of prenylation enzymes.

With reference to FIG. 7A, an exemplary method 200 of screening for prenylation enzyme inhibitors includes: providing a prenylation reaction group including a prenylation enzyme, an unnatural substrate to the prenylation enzyme having a unique moiety or a precursor to the unnatural substrate, and an antibody that recognizes the unique moiety 202; preparing a sample containing at least one protein capable of being prenylated, the prenylation enzyme, the unnatural substrate, and a candidate prenylation enzyme inhibitor 204; allowing contents of the sample to interact 206; detecting the resulting prenylated proteins in the sample using the antibody 208; and identifying the candidate prenylation enzyme inhibitor as an actual prenylation enzyme inhibitor when the detected prenylated proteins are below a predetermined level 210.

With regard to the step in the exemplary method of providing a prenylation reaction group 202 various prenylation reaction groups containing different prenylation enzymes, unnatural substrates (or precursors), and antibodies may be provided without departing from the spirit and scope of the present invention, so long as the selected unnatural substrate is an unnatural substrate of the selected prenylation enzyme, and selected unnatural substrate has a unique moiety that is recognized by the selected anibody. For example, components of the prenylation reaction group may be selected from a Group identified in Table 1, such as Group 1, wherein the prenylation enzyme is FTase, the unnatural substrate is AGPP, and the antibody is Anti-AG. For another example, components of the prenylation reaction croup may be selected from group 13 of Table 1, wherein the prenylation enzyme is GGTaseI, the unnatural substrate is NAFPP, and the antibody is Anti-NAG. Components taken from any discrete group of Table 1 are components of the prenylation reaction group that can be used in the exemplary method.

With regard to the step in the exemplary method of preparing a sample 204, the sample includes the prenylation enzyme, the unnatural substrate, at least one protein, and a candidate prenylation enzyme inhibitor. Because it may be desirable to limit the variables associated with practicing the screening method, it is preferred that the at least one protein be a protein that is known to be capable of being prenylated.

Once the sample has been prepared, the contents are allowed to interact with one another 206 before the resulting prenylated proteins in the sample are detected 208 using any immunodetection method known to those skilled in the art. The candidate prenylation enzyme inhibitor is identified as an actual prenylation enzyme inhibitor when the detected prenylated proteins are below a predetermined level. The predetermined level may be identified, for example, by quantifying the detected prenylated proteins using methods known to those skilled in the art and comparing the quantified prenylated protein levels to a standard curve plotting levels of prenylated proteins as a function of enzyme inhibition. For another example, the predetermined level may be identified using a control sample that does not contain the candidate inhibitor. In this regard, when a control sample that does not contain the candidate inhibitor is examined concurrently with a test sample that contains the candidate inhibitor, the candidate inhibitor is identified as an actual inhibitor when the detected presence of prenylated proteins in the test sample is less than the detected presence of prenylated proteins in the control sample.

Additional samples may be prepared, which additional samples can be examined concurrently with and compared to the first sample. For example, a first sample may be provided with a first concentration of the candidate prenylation enzyme inhibitor and additional samples may be provided with additional concentrations of the candidate prenylation enzyme inhibitor. Further samples may be prepared, for example, as controls, which controls can be examined concurrently with the other samples. Controls could include, for example, a sample that is allowed to interact with the prenylation enzyme and the candidate prenylation enzyme inhibitor, but not the unnatural substrate or precursor. Of course, various modifications to the exemplary method are contemplated and will become apparent to those skilled in the art from consideration of the present specification.

Figure 7B:
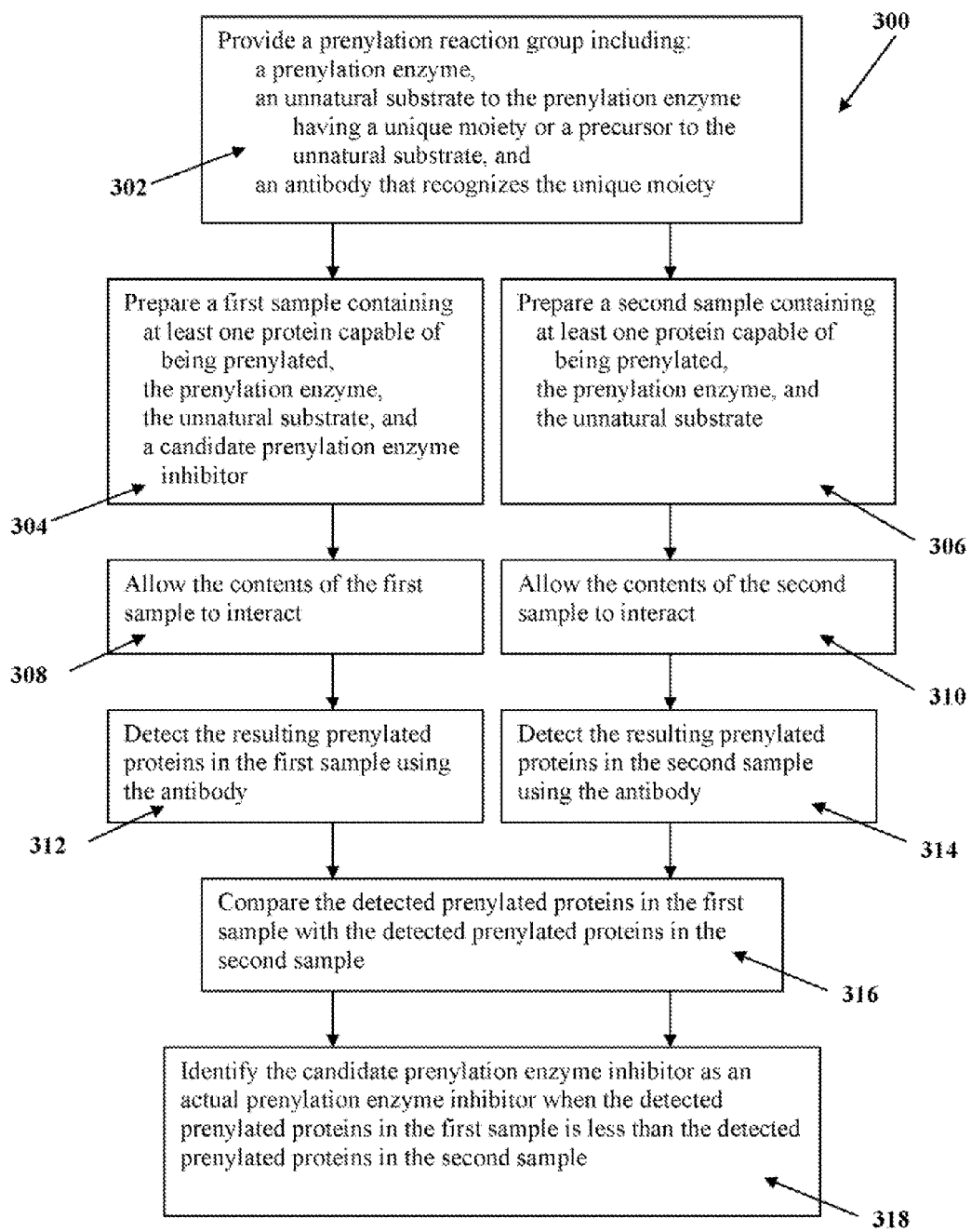
FIG. 7B is a flow chart illustrating the steps involved in another exemplary method for screening for inhibitors of prenylation enzymes.

With reference to FIG. 7B, another exemplary method 300 of screening for prenylation enzyme inhibitors includes: providing a prenylation reaction group including a prenylation enzyme, an unnatural substrate to the prenylation enzyme having a unique moiety or a precursor to the unnatural substrate, and an antibody that recognizes the unique moiety 302; preparing a first sample containing at least one protein capable of being prenylated, the prenylation enzyme, the unnatural substrate, and a candidate prenylation enzyme inhibitor 304; preparing a second sample containing at least one protein capable of being prenylated, the prenylation enzyme, and the unnatural substrate 306; allowing the contents of the first sample to interact 308; allowing the contents of the second sample to interact 310; detecting the resulting prenylated proteins in the first sample using the antibody 312; detecting the resulting prenylated proteins in the second sample using the antibody 314; comparing the detected prenylated proteins in the first sample with the detected prenylated proteins in the second sample 316; and identifying the candidate prenylation enzyme inhibitor as an actual prenylation enzyme inhibitor when the detected prenylated proteins in the first sample are less than the detected prenylated proteins in the second sample 318.

The exemplary method set forth in FIG. 7B is similar to the method set forth in FIG. 7A, except that there is a second sample expressly prepared, which second sample does not contain the candidate prenylation enzyme inhibitor 306. In this regard, after the contents of each sample are allowed to interact 308, 310, the resulting prenylated proteins in the samples are detected 312, 314 and compared 316. The detected prenylated proteins may be compared, for example, by quantifying the detected prenylated proteins in each sample by methods known to those skilled in the art, and comparing the quantified values. If the detected prenylated proteins in the second sample are greater than the detected prenylated proteins in the first sample, the candidate prenylation enzyme inhibitor may be identified as an actual inhibitor 318. Of course, various modifications to the exemplary method are contemplated and will become apparent to those skilled in the art from consideration of the present specification.

The present invention is further illustrated by the following specific but non-limiting examples. The following examples are prophetic, notwithstanding the numerical values, results and/or data referred to and contained in the examples.

EXAMPLES

Example 1

Procedures

All reactions are conducted under dry argon and stirred magnetically, except as noted. Reaction temperatures refer to the external bath temperatures. Analytical TLC is performed on precoated (0.25 mm) silica gel 60F-245 (Merck) plates and developed with given solvent conditions. Visualization is achieved by UV irradiation, iodine or by subjecting the plates to a 15% sulfuric acid, 1% ceric ammonium sulfate, 2% Molybdic anhydride solution followed by heating. Flash chromatography is performed on Merck silica gel 60 (230-400 mesh ASTM). All chromatography solvents are purchased from VWR (EM Science-Omnisolv high purity) and used as received. All reagents are purchased from Aldrich or Alfa Aesar. NMR Spectra are obtained in $CDCl_3$ (unless otherwise noted) at 200 or 400 MHz. Chemical shifts for the following deuterated solvents are reported in ppm downfield using the indicated reference peaks: $CDCl_3$ ($CDCl_3$ internal peak 7.27 ppm for $^1H$, 77.4 ppm for $^{13}C$). ESI-MS are performed at the University of Kentucky Mass Spectra Facility.

Reference is made herein to the synthesis set forth in Scheme 1, and to the compounds contained in Scheme 1, identified by the numerals 1a-7b.

Scheme 1: Synthesis of Analogue-Modified Haptens*

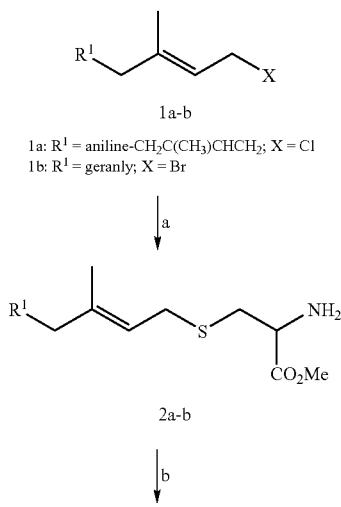

1a-b
1a: $R^1$ = aniline-$CH_2C(CH_3)CHCH_2$; X = Cl
1b: $R^1$ = geranly; X = Br ↓a 2a-b ↓b

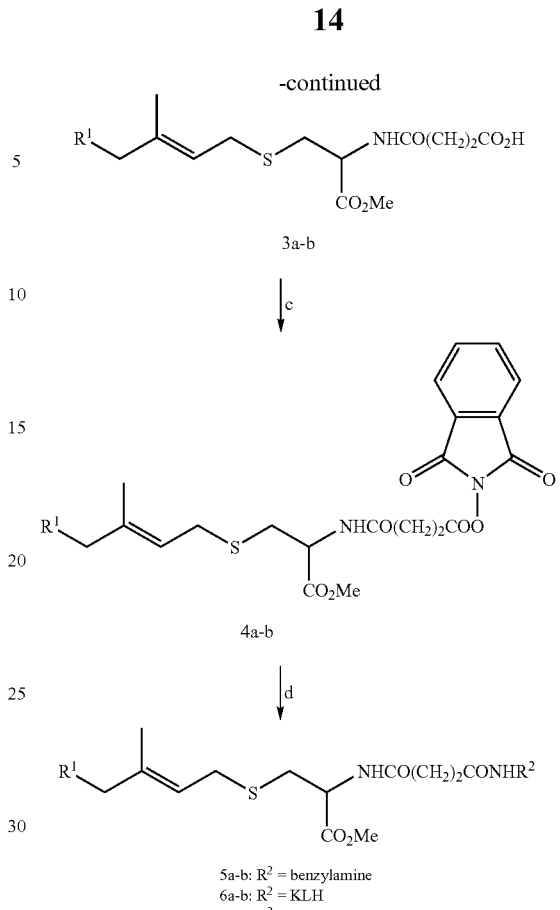

3a-b

↓c 4a-b

↓d 5a-b: $R^2$ = benzylamine
6a-b: $R^2$ = KLH
7a-b: $R^2$ = BSA

*Reagents:
(a) Cysteine methyl ester HCl, $NH_3$/MeOH, 0° C.
(b) Succinic anhydride, THF/$CH_2Cl_2$.
(c) N-Hydroxyphthalimide, CDI, MeCN.
(d) $R^2$, $NaHCO_3$(aq)/MeCN.

Anilinogeranyl Cysteine Methyl Ester 2-amino-3-(3,7-dimethyl-8-phenylamino-octa-2,6-dienylsulfanyl)-propionic Acid Methyl Ester (2a)

Chloride 1a is prepared from the corresponding alcohol (734 mg, 3.0 mmols) in 10 mL of acetonitrile as previously described in Chehade, et al. (2002) *J Am Chem Soc* 124, 8206-19. A solution of L-cysteine methyl ester hydrochloride (1.13 g, 6.50 mmols) in 20 mL of 7 M $NH_3$/MeOH is added to the cooled solution (−20° C.) of chloride 1a. The reaction initially forms a white precipitate which disappears. After 3 hours, the reaction mixture is allowed to warm to room temperature over one hour. The reaction mixture is partitioned between ether and water and extracted with ether (3X). The combined organic extracts are then dried over $MgSO_4$ and solvent is evaporated. Purification by flash chromatography (1:2:8) i-Pr-OH:EtOAc:Hexane yields 625 mg (60%) of a Yellow oil. Rf=0.32 in 1:2:5 i-Pr-OH:EtOAc:Hexane $^1H$ NMR ($CDCl_3$, 200 MHz) 7.10 (t, 2H, J=8.0 Hz), 6.63 (t, 1H, J=7.2 Hz), 6.55 (d, 2H, J=8.0 Hz) 5.39 (t, 1H, J=8.0 Hz), 5.23 (t, 1H, J=8 Hz), 3.75 (s, 3H), 3.59 (m, 3H), 3.13 (m, 2H), 2.86-2.95 (2d, 1H), 2.65-2.76 (2d, 1H), 2.06-2.19 (m, 4H), 1.63 (s, 3H), 1.62 (s, 3H) $^{13}C$ NMR ($CDCl_3$, 50 MHz) 174.58, 148.77, 139.42, 132.96, 129.38, 125.75, 120.53, 117.39, 113.08, 54.51, 52.49, 51.96, 39.50, 36.61, 30.14, 26.30, 16.33, 14.98; MS: (ESI, +) (M−H+) 363

Nitroanilinogeranyl Cysteine Methyl Ester 2-amino-3-[3,7-dimethyl-8-(4-nitro-phenylamino)-octa-2,6-dienylsulfanyl]-propionic Acid Methyl Ester (2b)

Purification by flash chromatography (3:2:5 i-Pr-OH:EtOAc:Hexane) yielded 276 mg (60%) of a yellow/brown oil. Rf=0.28 (3:2:5 i-Pr-OH:EtOAc:Hexane) 1H NMR (CDCl3, 400 MHz) 8.65 (d, 2H, J=8.0 Hz), 6.52 (d, 2H, J=8.0 Hz), 5.34 (t, 1H, J=12 Hz), 5.20 (t, 1H, J=16 Hz), 3.75 (s, 3H), 3.71 (s, 2H), 3.65 (m, 1H), 3.17 (d, 2H, J=16 Hz), 2.84-2.93 (2d, 1H), 2.64-2.75 (2d, 1H) 2.18 (t, 2H), 2.02(t, 2H) 1.22 (s, 3H), 1.19 (s, 3H) 13C NMR (CDCl3, 50 MHz) 174.80, 153.92, 139.04, 131.14, 126.60, 120.79, 111.40, 54.48, 52.52, 50.99, 39.25, 36.79, 30.25, 25.98, 25.61, 16.26, 14.92; MS: (ESI, +) (M−H+) 408

Farnesyl Cysteine Methyl Ester 2-amino-3-(3,7,11-trimethyl-dodeca-2,6,10-trienyl-sulfanyl)-propionic Acid Methyl Ester (2b)

Into a 100 mL round bottomed flask at 0° C. is added L-Cysteine methyl ester (1.38 g, 10.2 mmols) in 60 mL of 7M $NH_3$/MeOH. Neat farnesyl bromide (1b) (1.00 g 3.52 mmols) is then added and the solution is stirred at 0° C. for four hours. The reaction mixture is partitioned between ether and water and extracted 3× with ether, extracts are combined, dried over $MgSO_4$ filtered and evaporated. Purification by flash chromatography (1% MeOH:CHCl$_3$) yields 881 mg (74%) of a clear oil. Rf=0.22 in 5% MeOH in CHCl$_3$. $^1$H NMR (CDCl$_3$, 400 MHz): 5.24 (t, 1H, J=8 Hz), 5.10 (m, 2H), 3.75 (s, 3H), 3.64 (q, 1H), 3.10-3.25 (m, 2H), 2.86-2.91 (2d, 1H), 2.65-2.71 (2d, 1H), 2.04-2.10 (m, 6H), 2.04(m, 6H) 2.0 (t, 2H), 1.69 (s, 3H), 1.68 (s. 3H), 1.60 (s, 6H); $^{13}$C NMR (CDCl$_3$, 50 MHz) 174.93, 139.91, 135.71, 131.62, 124.69, 124.11, 120.35, 54.64, 52.35, 39.93, 36.77, 30.15, 26.98, 26.67, 25.86, 17.86, 16.33, 16.21 MS: (ESI, +) (M−H+) 340

General Conditions for Succinylation (3a-b)

Cysteine methyl ester 2b (881 mg, 2.6 mmols) is diluted in 20 mL of 1:1 THF:CH$_2$Cl$_2$ in a 100 mL round bottomed flask. Succinic anhydride (280 mg, 2.8 mmols) is then added and the mixture stirred for 4 hours, followed by evaporation of solvent. The residue is diluted in ether, washed sequentially with water and brine and then dried over sodium sulfate and concentrated in vacuo.

Anilinogeranyl Cysteine Succinate

N-[2-(3,7-dimethyl-8-phenylamino-octa-2,6-dienyl-sulfanyl)-1-methoxycarbonyl-ethyl]-succinamic Acid (3a)

Cysteine methyl ester 2a (302 mg, 0.83 mmols) provides 250 mg (65%) of succinate 3a as a white solid. Purification by flash chromatography (1:4:5:0.1 i-Pr-OH:EtOAc:hexane: acetic acid) Rf=0.32 (1:4:5 i-Pr-OH:EtOAc:Hexane.) $^1$H NMR (CDCl$_3$, 400 MHz) 7.12 (t, 2H, J=8.0 Hz), 6.65 (t, 2H, J=8.0 Hz), 6.58 (t, 2H), 5.34 (t, 1H, J=8.0 Hz) 5.14 (t, 1H, J=8.0 Hz), 4.75 (m, 1H), 3.72 (s, 3H), 3.60 (s, 2H), 3.11 (m, 2H), 2.79-2.93 (m, 2H), 2.65 (t, 2H, J=8.0 Hz), 2.52 (t, 2H, J=8 Hz), 2.11 (t, 2H, J=8 Hz) 2.02 (t, 2H, J=8 Hz), 1.63 (s, 3H), 1.62 (s, 3H); $^{13}$C NMR (CDCl$_3$, 50 MHz) 176.95, 171.84, 171.55, 148.48, 139.80, 132.79, 129.34, 125.86, 120.06, 117.68, 113.36, 52.91, 52.13, 39.42, 33.55, 30.69, 30.19, 29.53, 28.92, 26.22, 16.25, 14.96 MS: (ESI, +) (M−H+) 463

Nitroanilinogeranyl Cysteine Succinate

N-[2-[3,7-dimethyl-8(4-nitro-phenylamino)-octa-2,6-dienylsulfanyl]-1-methoxycarbonyl-ethyl]-succinamic Acid (3b)

Cysteine methyl ester 2b (339 mg, 0.83 mmols) provided 204 mg (57%) of succinate 3b as a yellow solid. Purification by flash chromatography (1:4:5:0.1) i-Pr-OH:EtOAc:hexane: acetic acid) Rf=0.3 (3:2:5) i-Pr-OH:EtOAc:hexane 1HNMR (CDCl3, 200 MHz): 8.03 (d, 2H, J=8.0 Hz), 6.49 (d, 3H), 5.30 (t, 1H, J=8 Hz), 5.11 (t, 1H, J=8 Hz), 4.75 (m, 1H), 3.77 (s, 3H), 3.74 (s, 2H), 3.10 (m, 2H), 2.81-3.02 (m, 2H), 2.57-2.76 (m, 4H), 2.06-2.19 (m, 4H), 1.67 (s, 3H), 1.64 (s, 3H); 13C NMR (CDCl3, 50 MHz): 176.20, 172.00, 171.50, 153.91, 139.60, 131.17, 126.83, 126.61, 120.39, 111.60, 52.92, 52.33, 51.14, 39.20, 33.65, 30.70, 30.28, 29.42, 26.01, 16.18, 14.80 MS: (ESI, +) (M−H+) 508

Farenesyl Cysteine Succinate

N-[1-methoxycarbonyl-2-(3,7,11-trimethyl-dodeca-2,6,10-trienylsulfanyl)-ethyl]-succinamic Acid (3b)

Cysteine methyl ester 2b (881 mg, 2.6 mmols) provides 937 mg (82%) of succinate 3b as a white solid. Puification by flash chromatography (1:2:7 i-Pr-OH:EtOAc:hexane) $^1$H NMR (CDCl$_3$, 400 MHz) 10.55 (bs, 1H), 6.72 (d, 1H, J=8 Hz), 5.17 (t, 1H, J=8 Hz), 5.07 (m, 2H), 4.75-4.80 (q, 1H), 3.73-3.73 (s, 3H), 3.13 (m, 2H), 2.90-2.94 (m, 1H), 2.80-2.85 (m, 1H), 2.69 (t, 2H), 2.57 (t, 2H), 1.92-2.08 (m, 8H), 1.65 (s, 3H), 1.64 (s, 3H), 1.57 (s, 6H); $^{13}$C NMR (CDCl$_3$, 100 MHz) 177.40, 171.90, 171.64, 140.17, 135.44, 131.38, 124.44, 124.38, n123.85, 123.78, 119.60, 119.55, 52.80, 52.75, 52.01, 51.97, 39.79, 39.72, 33.28, 31.67, 30.55, 29.96, 29.39, 26.80, 26.51, 25.79, 22.74, 17.78, 16.19, 16.10; MS: (ESI, +) (M−H+) 438

General Conditions for Activated Ester Formation (4a-b)

Succinamic acid 3c (59.6 mg, 0.126 mmols) is dissolved in 10 mL of dry acetonitrile in a 100 mL round-bottomed flask. Carbonyldiimidazole (26.4 mg 0.163 mmols) is then added and the mixture is allowed to stir for 5 minutes. N-hydroxypthalimide (26.4 mg, 0.163 mmols) is added and the solution is stirred for 1.5 hours. The solvent is then evaporated.

Anilinogeranyl Cysteine Succinyl Phthalimide

N-[2-(3,7-dimethyl-8-phenylamino-octa-2,6-diensulfanyl)-1-methoxycarbonyl-ethyl]-succinamic Acid 1,3-dioxo-1,2-;dihydro-isoindol-2-yl Ester (4a)

Succinate 3a (30 mg, 0.07 mmols) provides 25 mg (63%) of phthalimide 4a as a yellow/brown oil. Purified by column chromatography (CHCl$_3$). Rf=0.28 (1:1) Hexane:EtOAc $^1$H NMR (CDCl$_3$, 400 MHz): 7.88 (q, 2H), 7.78 (q, 2H), 7.16 (t, 2H), 6.68 (t, 1H), 6.60 (d, 2H), 6.37 (d, 1H), 5.37 (t, 1H), 5.17 (t, 1H), 4.83 (m, 1H), 3.76 (s, 3H), 3.63 (s, 2H), 3.15 (m, 2H), 3.06 (t, 2H), 2.92 (m, 2H), 2.71 (t, 2H), 2.03-2.18 (m, 4H), 1.67 (s, 3H), 1.65 (s, 3H); $^{13}$C NMR (CDCl$_3$, 50 MHz): 171.43, 169.94, 169.12, 161.93, 148.70, 139.79, 134.06, 132.89, 129.34, 125.72, 124.19, 120.08, 117.38, 113.07, 52.86, 52.10, 51.97, 39.43, 33.64, 30.63, 30.21, 26.78, 26.25, 16.26, 14.94 MS: (ESI, +) (M−H+) 608

Nitroanilinogeranyl Cysteine Succinyl Phthalimide

N-[1-[3,7-Dimethyl-8-(4-nitro-phenylamino)-octa-2,6-diensulfanyl]-1-methoxycarbonyl-ethyl]-succinamic Acid 1,3-dioxo-1,3-dihydro-isoindol-2-yl Ester (4b)

Succinate 3b (38 mg, 0.08 mmols) provided 41 mg (85%) of phthalimide 4b as a yellow oil. Purified by column chromatography (CHCl3). Rf=0.12 (1:1) Hexane:EtOAc 1H NMR (CDCl3, 400 MHz) 8.02 (d, 2H), 7.84 (q, 2H), 7.75 (q, 2H), 6.54 (d, 2H), 6.36 (d, 1H), 5.30 (t, 1H), 5.11 (t, 1H), 4.78 (q, 1H), 3.73 (s, 3H), 3.70 (s, 2H), 3.10 (t, 2H), 3.02 (t, 2H), 2.80-2.98 (m, 2H), 2.69 (t, 2H), 2.11 (m, 2H), 2.00 (t, 2H), 1.63 (s, 3H), 1.59 (s, 3H); 13C NMR (CDCl3 100 MHz) 171.36, 169.17, 161.94, 153.85, 146.06, 139.44, 138.02, 135.02, 131.06, 129.03, 126.60, 126.56, 124.21, 120.32, 111.40, 52.95, 52.24, 51.02, 39.21, 33.60, 30.62, 30.24, 27.02, 26.75, 26.00, 16.22, 14.87

Farnesyl Cysteine Succinyl Phthalimide

N-[1-methoxycarbonyl-2-(3,7,11-trimethyl-dodeca-2,6,10-trienylsulfanyl)-ethyl]-succinamic Acid 1,3-dioxo-1,2-dihydro-isoindol-2-yl Ester (4b)

Succinate 4b (60 mg, 0.14 mmols) provides 80 mg (58%) of phthalimide 5b as a brown oil. Purified by column chromatography (CHCl$_3$). Rf=0.3 (1:1) Hexane:EtOac $^1$H NMR (CDCl$_3$, 400 MHz) 7.88 (q, 2H), 7.79 (q, 2H), 6.38 (d, 1H), 5.20(t, 1H), 5.09 (t, 2H), 4.82 (m, 1H), 3.76 (s, 3H), 3.74 (s, 2H), 3.11-3.22 (m, 2H), 3.07 (t, 2H), 2.86-3.00 (m, 2H), 2.74 (t, 2H), 1.95-2.10 (m, 8H), 1.68 (s, 3H), 1.66 (s, 3H), 1.60 (s, 6H); $^{13}$C NMR (CDCl$_3$, 100 MHz) 171.44, 169.90, 169.93, 161.91, 140.29, 135.57, 134.96, 131.53, 129.06, 124.50, 124.19, 123.90, 119.64, 52.85, 52.00, 39.88, 39.81, 33.54, 30.62, 30.14, 29.03, 28.23, 26.90, 26.75, 26.59, 25.90, 17.89, 16.31, 16.21.

General Conditions for Benzylamine Coupling (5a-b)

Phthaimide 4b (47.2 mg, 0.08 mmols) is dissolved in 1 mL of acetonitrile and 5 mL of 5% NaHCO$_3$ buffer pH=9 in a 25 mL RB flask. Benzylamine (17.3 mg, 0.16 mmols) is then added and the reaction is allowed to stir for 1.5 hours at room temperature. 10 mL of water is added and organics are extracted with ether (3×), dried over MgSO$_4$, and organic solvent evaporated.

Anilinogeranyl Benzyl Amine 2-(3-Benzylcarbamoyl-propionylamino)-3-(3,7-dimethyl-8-phenylamino-octa-2,6-Dienylsulfanyl)-propionic Acid Methyl Ester (5a)

Phthalimide 4a (133 mg, 0.22 mmols) provides 59 mg (48%) of amide 5a as a white solid. Purification by column chromatography (3:7) Hexane:EtOAc. $^1$H NMR (CDCl$_3$, 400 MHz) 7.21-7.31 (m, 5H), 7.12 (t, 2H), 6.55-6.66 (m, 4H), 6.23 (bt, 1H), 5.34 (t, 1H), 5.14 (t, 1H), 4.71 (q, 1H), 4.38 (d, 2H, J=6 Hz), 3.70 (s, 3H), 3.59 (bs, 2H), 3.10 (m, 2H), 2.76-2.91 (m, 2H), 2.50-2.61 (m, 4H), 1.99-2.13 (m, 4H), 1.63 (s, 3H), 1.62 (s, 3H) $^{13}$C NMR (CDCl$_3$, 50 MHz): 171.23, 171.94, 171.46, 148.63, 139.77, 138.41, 132.84, 129.42, 129.34, 129.19, 128.94, 128.87, 128.08, 127.93, 127.73, 125.74, 120.08, 117.411, 113.10, 52.82, 52.09, 51.963, 43.85, 39.45, 33.50, 31.71, 31.66, 30.12, 26.25, 16.28, 14.95 MS: (ESI, +) (M−H+) 552

Nitroanilinogeranyl Benzyl Amine 2-(3-Benzylcarbamoyl-propionylamino)-3-[3,7-dimethyl-8(4-nitro-phenylamino)-octa-2,6-dienylsulfanyl]-propionic Acid Methyl Ester (5b)

Phthalimide 4b (13 mg, 0.02 mmols) provided 9 mg (76%) of amide 5b as a yellow solid. Purification by column chromatography (3:4) Hexane:EtOAc. 1HNMR (CDCl3, 400 MHz) 8.01 (d, 2H, J=9.2 Hz), 7.20-7.29 (m, 5H), 6.69 (d, 1H, J=7.6 Hz), 6.48 (d, 2H, J=9.2 HZ), 6.26 (t, 1H), 5.30 (t, 1H), 5.12 (t, 1H), 4.96 (t, 1H), 4.68-4.72 (m, 1H), 4.38 (d, 2H, J=5.6 Hz), 3.70 (s, 3H), 3.68 (d, 2H, J=5.6 Hz), 3.10 (m, 2H), 2.77-2.91 (m, 2H), 2.51-2.62 (m, 4H), 2.10-2.16 (t, 2H), 2.00-2.03 (t, 2H), 1.62 (s, 3H), 1.60 (s, 3H); 13C NMR (CDCl3, 50 MHz): 172.22, 171.92, 171.41, 153.89, 139.39, 138.33, 131.04, 128.88, 127.91, 127.67, 126.56, 120.33, 111.38, 52.86, 52.21, 50.99, 43.88, 39.22, 33.59, 31.67, 31.65, 30.22, 26.00, 16.24, 14.87 MS: (ESI, +) (M−H+) 597

Farnesyl Benzylamine 2-(3-Benzylcarbamoyl-propionylamino)-3-(3,7,11-trimethyl-dodeca-2,6,10-trienylsulfanyl)propionic Acid Methyl Ester (5b)

Phthalimide 5b (47 mg, 0.08 mmols) provides 42 mg (67%) of amide 6b as a white solid. Purification by column chromatography (4:6) Hexane:EtOAc. $^1$H NMR (CDCl$_3$, 400 MHz) 7.25-7.34 (m, 5H), 6.623 (d, 1H), 6.28 (t, 1H), 5.20 (t, 1H), 5.09 (t, 2H), 4.75 (q, 1H), 4.44 (d, 2H), 3.75 (s, 3H), 3.09-3.22 (m, 2H), 2.81-2.96 (m, 2H), 2.55-2.67 (m, 4H), 1.96-2.13 (m, 8H), 1.68 (s, 3H), 1.67 (s, 3H), 1.60 (s, 6H); $^{13}$C NMR (CDCl$_3$, 50 MHz): 172.21, 171.94, 171.47, 140.29, 138.44, 135.60, 131.54, 128.87, 127.94, 127.64, 124.53, 123.93, 119.72, 52.79, 52.07, 43.89, 39.92, 39.84, 33.47, 31.77, 31.73, 30.12, 26.95, 26.66, 25.91, 17.90, 16.36, 16.23; MS: (ESI, +) (M−H+) 529

General Conditions for Protein Coupling (6a-b and 7a-b)

Phthalimido esters (4a-b) are dissolved in 6 mL of 1:5 acetonitrile and 5% NaHCO$_3$ in a 100 mL pear-shaped flask. BSA (7) (0.1 mL of 10 mg/mL solution in phosphate buffered saline (PBS) pH 7.2) or KLH protein (6) (3 mL of 10 mg/mL solution in PBS pH 7.2) is added and stirred vigorously for 2 hours or until analysis by TLC in 1:1 hexane:EtOAc shows no residual activated phthalimide ester spot. The solution is dialyzed overnight in 20% DMSO, PBS pH 7.5 then PBS (3×1 L, 6 hrs each).

Antibody Generation

Hapten protein conjugates 6a and 6b are used to immunize rabbits subcutaneously by emulsifying 1.5 mg of each conjugate with Freund's complete adjuvant. This is followed by six secondary boosters of the same dose with incomplete Freund adjuvant at intervals of 14 days. The rabbits are bled 10 days after each boost. Blood is allowed to coagulate overnight in 50 mL centrifuge tubes and sera is collected and stored at 0° C.

ELISA Screening

ELISA plates (96-well polystyrene) are coated with 100 uL per well of BSA conjugates or BSA (1 ug/mL) in PBS (pH=7.6) and incubated for 1 hr at 37° C. The plates are then washed thoroughly with 10% Tween in PBS buffer (PT) (pH=7.4). 150 uL of serum diluted 1:100 in PT buffer containing casein (PCT) is added and diluted 1:3 down the plate, then incubated 1 hr at 37° C. The plates are washed with PT buffer and 100 uL of secondary antibody (1:10,000) is added to each well. The plates are incubated 1 hr at 37° C. and again washed. 100 uL of p-nitrophenylphosphate is added to each well (2 pills in 10 ml of Tris buffer ph=9.5). After 20 minutes color begins to develop and absorbance is read at 405 nm.

FTase Protein Substrate Modification

2 µg of recombinant bacterially expressed RDJ2 is incubated with 20 µM AGPP or FPP and 5 µg FTase in 50 µL of TrisHCl buffer (pH=7.4). See Andres, et al. (1997) *Arch Biochem Biophys* 346, 113-24. The reactions are incubated for 30 min at 37° C., boiled with SDS and PAGE performed using the protein concentrations indicated on the blots.

Cell Culture and Transient Transfection of GST-tagged Q61LH-Ras

HEK-293 cells are routinely sub-cultured twice weekly at a split ratio of 1:4 in DMEM containing 5% FBS to maintain exponential growth. Cells used for experiments are of passage number 0-20. HEK cells are seeded 24 hrs prior to transfection at 60-70% confluency onto poly-L-lysine coated plates. Monolayers of HEK cells are transiently transfected with 2 µg pEBG-H-Ras-Q61L or pEBG alone 35 mm dish using the calcium phosphate precipitation method as previously described in Berger, et al. (1992) *J Steroid Biochem Mol Biol* 41, 733-8. See also, Shi, et al. (2005) *Mol Cell Biol* 25, 830-46. The cells are harvested at 48 h, washed with 2×10 mL of PBS, lysed by sonication, and frozen at −70° C.

AGOH Labeling and FTI Inhibition of Label in HEK-293 Cells

Plates are coated with poly-L-Lysine and seeded with HEK-cells in Dulbecco's modified Eagle's medium with 5% fetal bovine serum. Cells are incubated in medium containing 30 µM lovostatin and 10 µM GGOH for 24 hrs. The media is poured off then replenished with media without lovostatin and GGOH and are treated with 3 µM FTI-277 (calbiochem), 20 µM GGTI-2147 (calbiochem) or no inhibitor and incubated at 37° C. for 1 hour. DMSO as a vehicle, or 100 µM AGOH is then added and incubated at 37° C. for two hours. Medium is then removed and cells are extracted into 300 µL PBS containing Protease Inhibitor cocktail set 1 (Calbiochem). The samples are sonicated and centrifuged for 5 minutes. The supernatant is removed and used for western blotting.

AGOH Incorporation into Unblocked Cells

Plates are coated with poly-L-Lysine and seeded with HEK-cells in Dulbecco's modified Eagle's medium with 5% fetal bovine serum. The cells ware then treated with DMSO as a vehicle, or 30 µM AGOH 5a is then added and incubated at 37° C. for the indicated time points. Medium is then removed and cells are extracted into 300 µL PBS containing Protease Inhibitor cocktail set 1 (Calbiochem). The samples are sonicated and centrifuged for 5 minutes. The supernatant is removed and used for western blotting.

Western Blot Analysis

Cells are harvested by scraping into 300 µl phosphate buffered saline containing protease inhibitor cocktail set 1 (calbiochem), followed by sonication on ice. Protein concentration is determined using a Bradford reagent kit (Pierce). The proteins from the FTase reaction mixtures or cell lysates are then separated using 12% SDS-polyacrylamide gels followed by transfer to nitrocellulose membranes. The membranes are incubated in blocking buffer PCT (see ELISA) for one hour at room temperature, after which the following steps are used: incubation with Anti-AG 1:1000 to 1:10,000 in PCT for one hour; 3×15 minute washes with vigorous shaking in PT buffer (see ELISA); incubation at room temperature one hour with goat anti-rabbit horseradish peroxidase-conjugated secondary antibody (Zymed) at a dilution of 1:20,000 in PCT buffer; and four 15 minute washes with PT buffer. The membranes are then subjected to enhanced chemiluminescence detection by incubation in 20 mL of detection buffer (Pierce Super Signal) for one minute.

Example 1

Results

Synthesis of Analogue Modified Antigen

The preparation of the prenyl analogue carrier protein conjugates 6a-b and 7a-b is outlined in Scheme 1, set forth above. The haptens are designed to mimic the C-terminal peptide of a fully processed prenylated protein that has undergone both endoproteolysis and carboxymethylation. Thioether 2a is obtained in 60-74% yield by addition of a solution of 1-cysteine methyl ester HCl in NH$_3$/MeOH to the previously described chloride 1a. The farnesyl thioether 1b is prepared by addition of farnesyl bromide 1b to 1-cysteine methyl ester HCl in NH$_3$/MeOH. Condensation of amines 2a-b with succinic anhydride in THF:CH$_2$Cl$_2$ afforded succinates 3a-b in 57%-85% yield after chromatography. See Berndt, et al. (1995) *JACS* 117, 9515-9522. Activated esters 4a-b are prepared from carboxylates 3a-b in 58%-85% yield by reaction with CDI followed by condensation with N-OH phthalimide. G. Yang, et al. (1996) *JACS* 118, 5881-5890. The N-hysdroxysuccimidyl (NHS) ester of a similar farnesyl hapten is reported to undergo an undesired intramolecular cyclization to an unreactive succinimide. In to the NHS ester, phthalimdies 4a-b are stable and show no evidence of intramolecular contrast to the NHS ester, phthalimdies 4a-b are stable and show no evidence of intramolecular cyclization. The suitability of phthalimdies 4a-b to form conjugates with carrier protein is modeled under conditions typical for coupling activated esters to lysine residues. Condensation of benzylamine with phthalimdies 4a-b in 1:5 Acetonitrile:5% NaHCO$_3$ give model amides 5a-b in 51%-76% yield.

With activated haptens in hand, anilinogeranyl, pNO$_2$anilinogeranyl and farnesyl immunoconjugates are generated. Phthalimides 4a-c are reacted with carrier proteins KLH and BSA to provide hapten conjugated proteins 6a-c (AG-KLH, NAG-KLH and F-KLH) and 7a-c (AG-BSA, NAG-BSA and F-BSA). BSA has approximately 32 reactive lysine residues and the extent of covalent modification of immunoconjugates 7a-c is quantified by measuring the remaining free amino groups relative to unmodified BSA. BSA, and each of the BSA conjugates 7a-b is reacted with trinitrobenzene sulfonate and the ratio of free amines in unmodified BSA to modified BSA is determined by UV absorbance at 335 nm. Habeeb (1966) *Anal. Biochem.* 14, 328. Fifty percent of the lysine residues in immunoconjugates 7a-b are modified by the activated esters 4a-b.

Generation of Anti-anilinogeranyl Antibodies

Figure 8A:
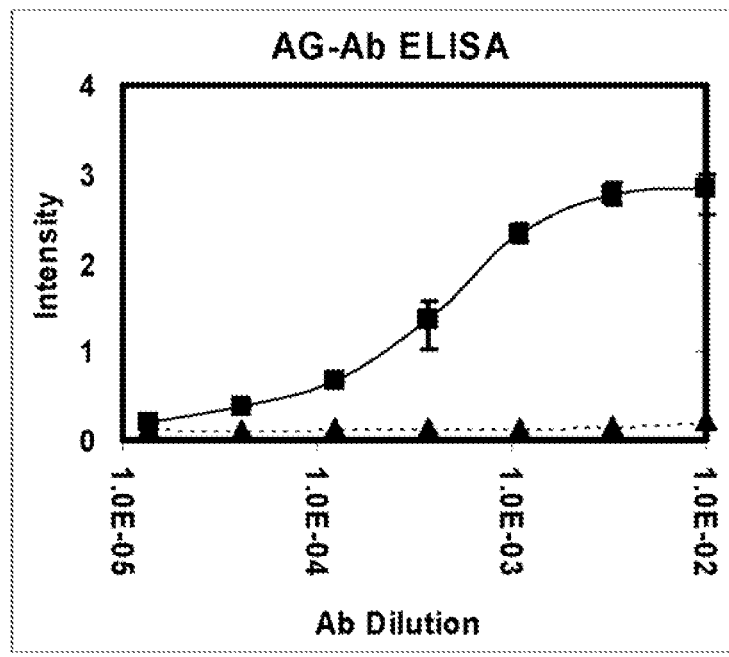
FIG. 8A is a graph showing the results of an ELISA assay of anilinogeranylated proteins reacted with antibodies of the present invention, showing the response of Anti-AG to an AG-modified protein (closed squares) and to an unmodified protein (closed triangles)
Figure 8B:
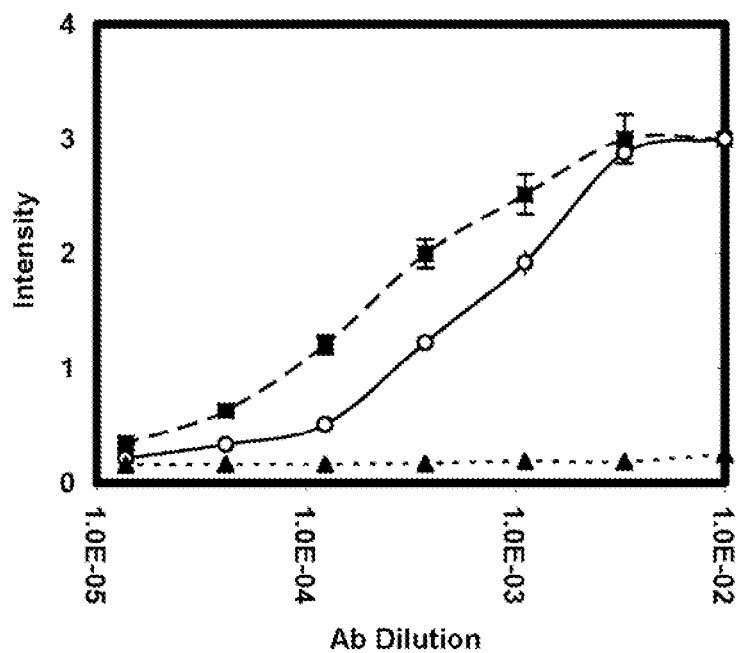
FIG. 8B is a graph showing the results of an ELISA assay of anilinogeranylated proteins reacted with antibodies of the present invention, showing the response of Anti-AG to an AG-modified protein (closed squares), to a NAG-modified protein (open circles), and to an unmodified protein (closed triangles)
Figure 8C:
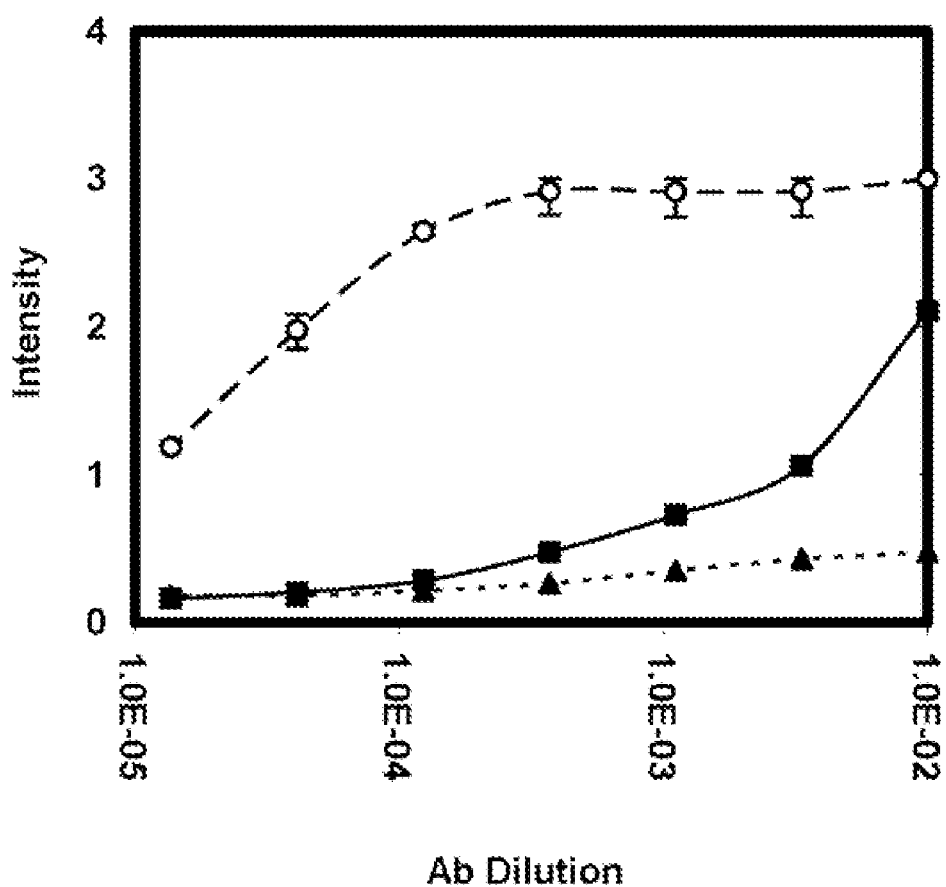
FIG. 8C is a graph showing the results of an ELISA assay of anilinogeranylated proteins reacted with antibodies of the present invention, showing the response of Anti-NAG to an AG-modified protein (closed squares), to a NAG-modified protein (open circles), and to an unmodified protein (closed triangles)

Polyclonal antibodies to the anilinogeranyl modification are prepared by immunizing rabbits with AG-KLH (6a) and NAG-KLH (6b). F-KLH (6c) elicits no immunogenic response. This is in agreement with previous reports in which attempts to prepare anti-farnesyl antibodies have resulted in weakly binding reagents that recognize both farnesyl and geranylgeranyl isoprenoid lipids. Due to the poor immune response to the F-KLH protein, (6b) attempts to prepare an anti-farnesyl antibody are abandoned. With reference to FIGS. 8A through 8C, polyclonal immune sera collected from the rabbits are screened using an enzyme linked immunosorbent assay (ELISA). No ELISA response is detected to unmodified BSA, AG-BSA (7a), or NAG-BSA (7b) in pre-immune sera. Sera antibodies raised against AG-KLH 6a (Anti-AG) and NAG-KLG 6b are able to bind to AG-BSA 7a and NAG-BSA 7b, respectively. There is cross-reactivity using the anti-AG antibody with the anilinogeranyl and pNO$_2$-anilinogeranyl-modified BSA proteins.

Specificity and Analysis of Anti-anilinogeranyl Antibodies

The antibodies generated are directed to proteins modified with cysteine methyl ester analogues of FPP; however, the actual antigen that is presented to the immune system is unknown as the ester may be hydrolyzed by enzymes in the whole animal. Additionally, it is possible that in vivo incorporation of unnatural analogues into proteins will alter the normal $Ca_1a_2X$ endoproteolysis and carboxymethylation steps. The utility of the polyclonal anilinogeranyl antibodies might well be limited if they only recognized the cysteine methyl ester form of modified proteins. Therefore, it is important to test the ability of these antibodies to recognize proteins modified by FTase with the anilinogeranyl moiety without subsequent endoproteolysis and carboxymethylation.

Figure 9A:
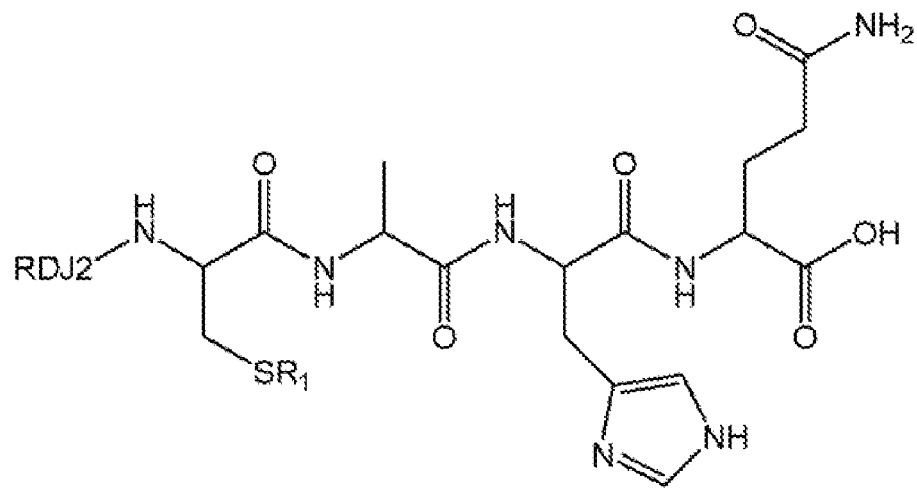
FIG. 9A is a chemical formula of a C-terminal portion of a modified RDJ2 Protein.
Figure 9B:
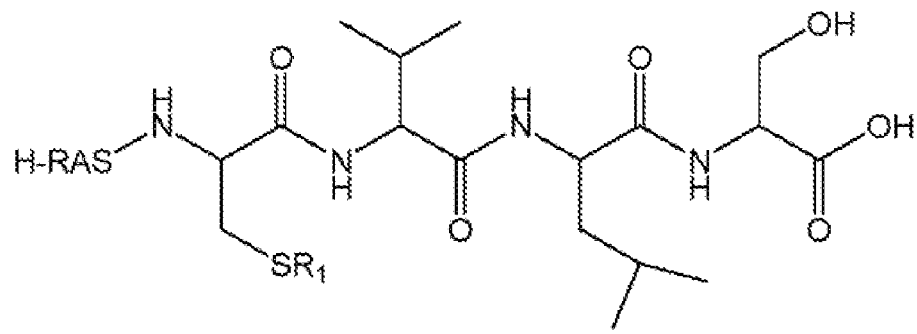
FIG. 9B is a chemical formula of a C-terminal portion of a modified RAS Protein.
Figure 10A:
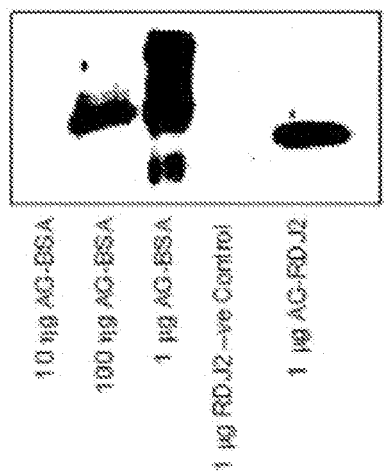
FIG. 10A depicts the results of a Western analysis of anilinogeranylated proteins and an unmodified protein probed with Anti-AG.
Figure 10B:
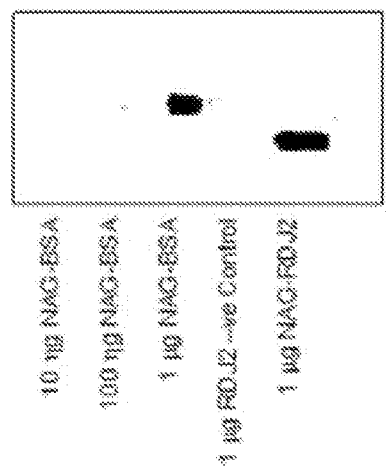
FIG. 10B depicts the results of a Western analysis of nitroanilinogeranylated proteins and an unmodified protein probed with Anti-AG.
Figure 10C:
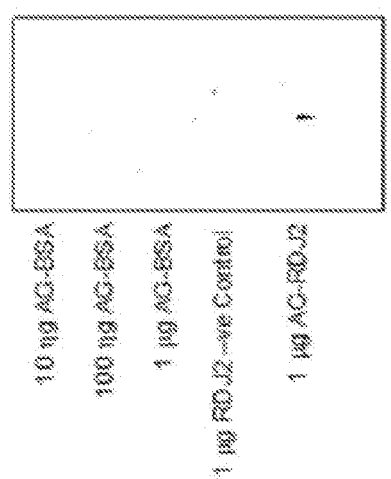
FIG. 10C depicts the results of a Western analysis of anilinogeranylated proteins and an unmodified protein probed with Anti-NAG.
Figure 10D:
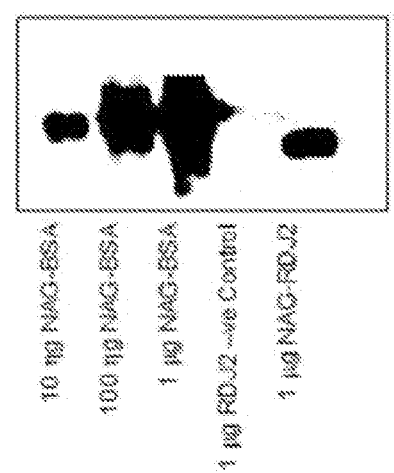
FIG. 10D depicts the results of a Western analysis of nitroanilinogeranylated proteins and an unmodified protein probed with Anti-NAG.

With reference to FIGS. 9A and 9B, bacterially expressed DNAJ-like RDJ2 and Q61L oncogenic H-Ras proteins contain the unfarnesylated and unprocessed CAHQ and CVLS $Ca_1a_2X$ motifs respectively. FTase catalyzed in vitro modification of these proteins with FPP, AGPP, and NAGPP provided lipid thioether-linked proteins with intact $Ca_1a_2X$ motifs. These reaction mixtures are then analyzed by western blot with Anti-AG and anti-NAG antibody sera. With reference to FIGS. 10A through 10D, Anti-AG is able to bind to AG-BSA and NAG-BSA derivatized by the methyl ester haptens as well as the AG-RDJ2 and NAG-RDJ2, but, show no reactivity to the unmodified RDJ2. Additionally, the antibodies are also unreactive towards farnesylated F-RDJ2 and F-Ras. Identical results are found when AG-Ras is examined (data not shown). Additionally, the antibodies are also unreactive towards farnesylated F-RDJ2 and F-Ras (data not shown). Similar results are found with the anti-NAG antibody except the anti-NAG antibody is more specific for the pNO$_2$-anilinogeranylated proteins over the anilinogeranylated proteins.

Figure 11A:
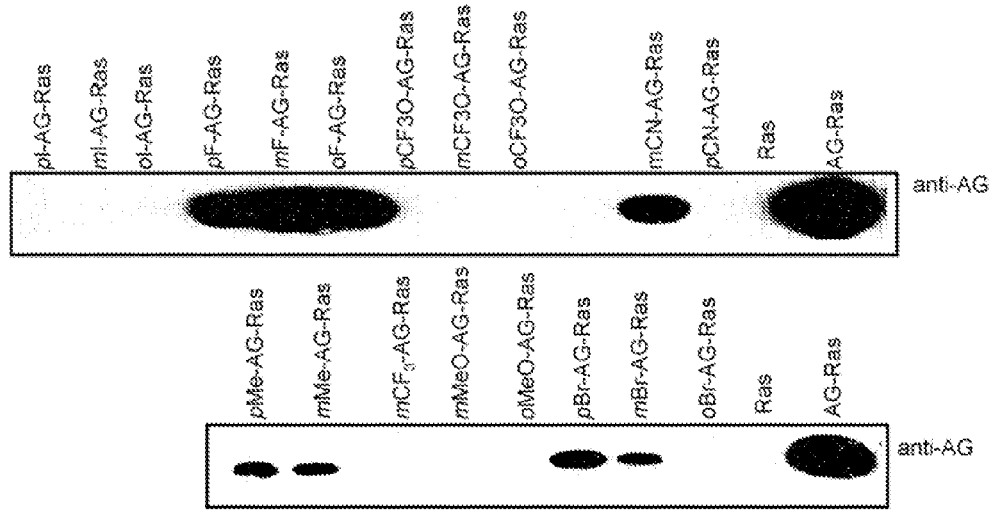
FIG. 11A depicts the results of a Western analysis of an unmodified protein and proteins modified with different unique moieties from unnatural substrates of FTase probed with Anti-AG.
Figure 11B:
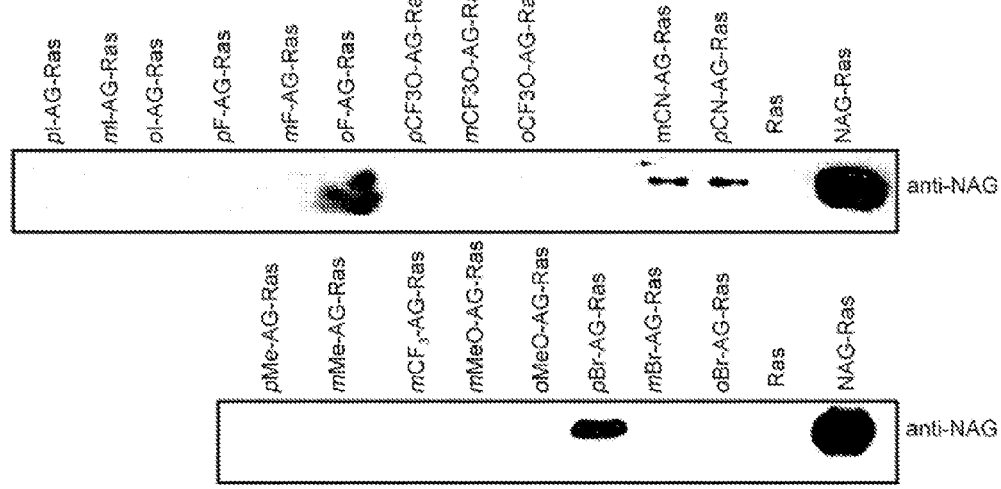
FIG. 11B depicts the results of a Western analysis of an unmodified protein and proteins modified with different unique moieties from unnatural substrates of FTase probed with Anti-NAG.

Since there is cross reactivity with the anti-AG antibody the ability of the anti-AG and anti-NAG antibodies to recognize other aniline analogs incorporated into proteins by FTase is tested. With reference to FIGS. 11A and 11B, H-Ras is reacted with the analogs pCN-AGPP, mCN-AGPP, oCF3O-AGPP, mCF3O-AGPP, pCF3O-AGPP, oF-AGPP, mF-AGPP, pF-AGPP, oI-AGPP, mI-AGPP, pI-AGPP, oBr-AGPP, mBr-AGPP, pBr-AGPP, oMeO-AGPP, mMeO-AGPP, mCF3-AGPP, mMe-AGPP, and pMe-AGPP. The anti-AG antibody is found to be less specific for the aniline substitution and is able to cross-react with the analogs containing small substitutions in the aniline ring of AGPP. This includes the mCN-AGPP, oF-AGPP, mF-AGPP, pF-AGPP, mBr-AGPP, pBr-AGPP, mMe-AGPP, and pMe-AGPP modified H-Ras proteins. The anti-NAG antibodies recognized the mCN-AGPP, pCN-AGPP, and pBr-AGPP-modified H-Ras proteins. These results suggested that the antibodies could be useful for many different anilinogeranyl diphosphate analogs not just the ones they are designed to recognize.

FTase Dependant Anilnogeraniol Incorporation into Cellular Proteins

Farnesol, geranylgeraniol and a number of farnesol analogues become incorporated into cellular proteins when added to the culture media of growing cells. See e.g., Crick, et al. (1995) *Biochem Biophys Res Commun* 211, 590-9; Crick, et al. (1997) *Biochem Biophys Res Commun* 237, 483-7. These compounds are thought to traverse the plasma membrane and act as a substrate for sequential kinase reactions to give FPP, GGPP or the diphosphate analogue which can be then be utilized by FTase or GGTaseI to appropriately modify cellular proteins. Thai, et al. (1999) *Proc Natl Acad Sci U S A* 96, 13080-5. The kinases involved in the phosphorylation reactions have been characterized in plants, but not in mammalian cells. In vitro, both FFP and AGPP are transferable by FTase to a CVLS substrate with similar kcat and Km values. See Chehade, et al. (2000) *J. Org. Chem.* 65, 3207-3033. It is thought that nilinogeraniol might also cross the plasma membrane of cells, be converted to the diphosphate and become incorporated into proteins by FTase. However, it is also possible that anilinogeraniol might be toxic to mammalian cells. Accordingly, the acute cytoxicity of anilinogeraniol is examined by incubating human embryonic kidney (HEK-293) cells with up to 100 µM anilinogeraniol for three days. Cells treated with anilinogeraniol show no morphological changes and no decrease in cell growth relative to controls at any of the concentrations tested (data not shown).

Figure 12:
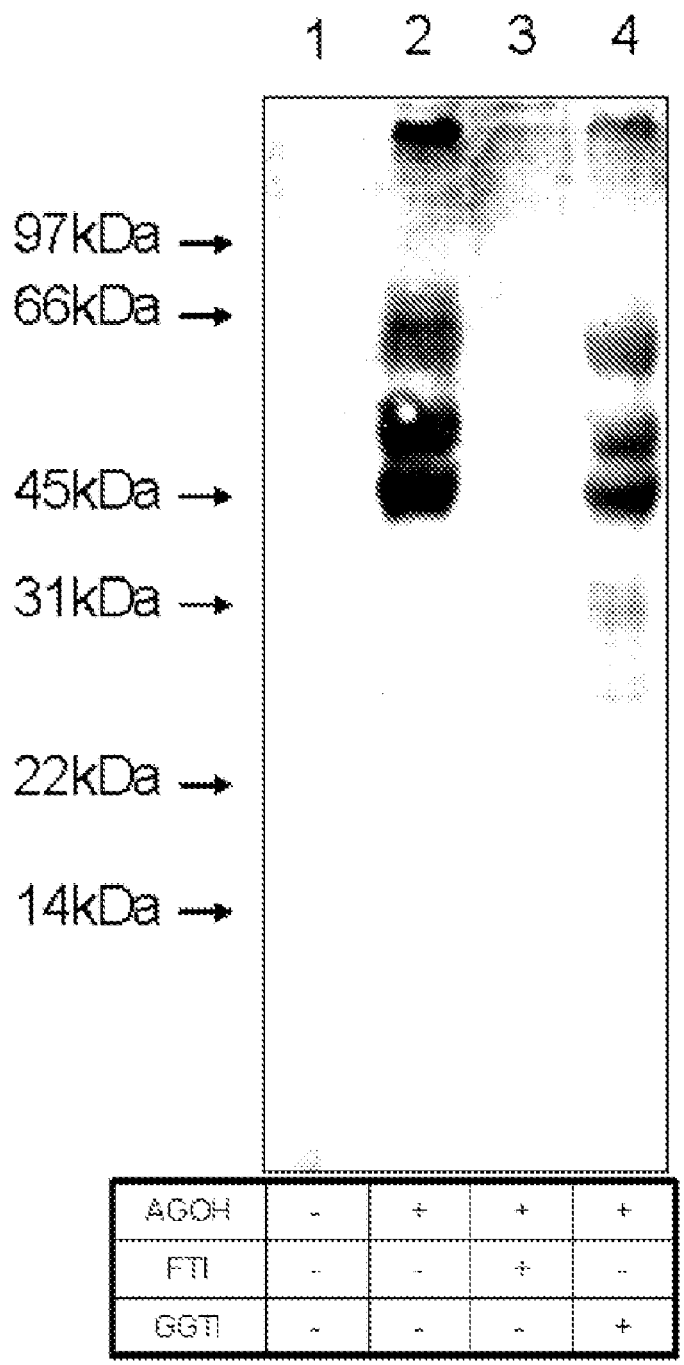
FIG. 12 depicts the results of a Western analysis of proteins extracted from cells that were incubated with anilinogeranyl alcohol, in the presence and absence of an FTase inhibitor and a GGTase Inhibitor, probed with Anti-AG.
Figure 13:
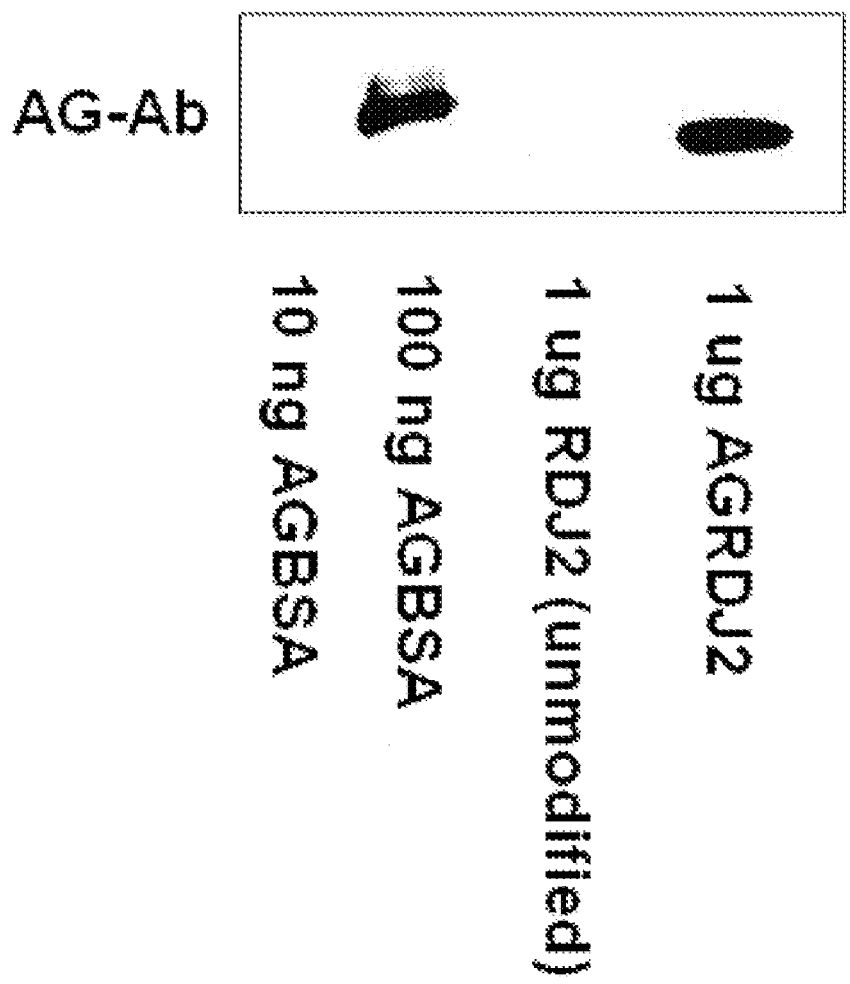
FIG. 13 depicts the results of a Western analysis of anilinogeranyl-modified proteins (lanes 1 and 2; protein modified in vitro with anilinogeranyl diphosphate lane 4), and an unmodified protein (lane 3)

The Anti-AG antibodies are used to probe extracts of HEK-293 cells incubated in the presence of AGOH to determine if the anilinogerarnyl group is incorporated into cellular proteins. These cells are initially blocked with lovostatin an upstream inhibitor of endogenous FPP and GGPP formation and treated with GGOH for the geranylgeranylation of proteins that play a role in cell survival. McGuire, et al. (1997) *Oncogene* 14, 305-12. FIG. 12 shows that there are numerous anilinogeranyl modified proteins in cells treated with AGOH, while no proteins are detected in the absence of the unnatural FPP analog. In order to determine whether the protein modification is FTase dependent, cells are incubated in the presence of AGOH and either the farnesyl transferase inhibitor FTI-277 or the geranylgeranyl transferase I inhibitor GGTI-2147. See Shi, et al. (2005) *Prostate* 62, 69-82; Lesh, et al. (2001) *Am J Physiol Lung Cell Mol Physiol* 281, L824-31. With reference to FIG. 13, lane 3 shows that no anilinogeranyl modified proteins are detected in the presence of the FTI. However, in the presence of the geranylgeranyl transferase I inhibitor, the pattern of proteins modified with anilinogeranyl moiety is similar to that without any inhibitor present. Some additional, lower molecular weight Anti-AG reactive bands appear when GGTaseI is inhibited. FTase catalyzed transfer of the anilinogeranyl lipid to protein is the most consistent explanation for these observations. This also suggest that FTase may be able to utilize AGPP to modify some normally geranylgeranylated proteins when GGTaseI is inhibited. This is not unreasonable, as the normally farnesylated K-Ras4B becomes geranylgeranylated in the presence FTIs. See Rowell, et al. (1997) *J Biol Chem* 272, 14093-7; Whyte, et al. (1997) *J Biol Chem* 272, 14459-64.

Figure 14:
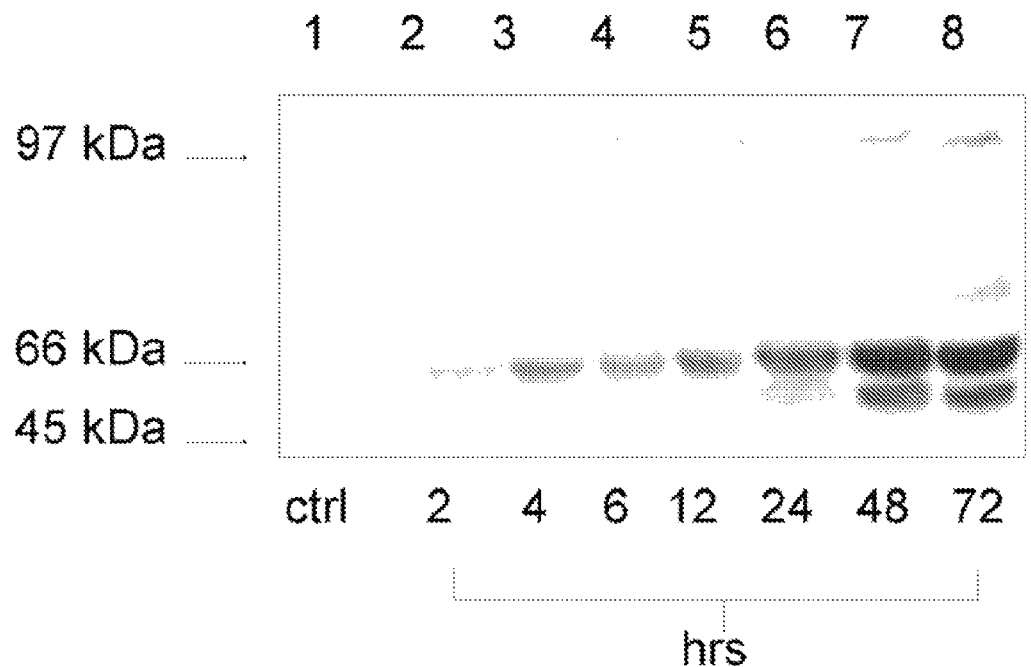
FIG. 14 depicts the results of a study wherein cells with no lovastatin blockade are incubated with anilinogeranyl alcohol for various amounts of time before extracting the cellular proteins, loading the samples onto an SDS-PAGE gel transferred to nitrocellulose, and immunodetecting the proteins using Anti-AG.

The AGOH analogue undergoes diphosphorylation to be incorporated into cellular proteins. This diphosphorylation may not be on time-scale that allows competitive modification of proteins in the presence of FPP. Cells are incubated without a lovastatin blockade on endogenous FPP formation with 30 μM AGOH and sampled every few hours. FIG. 14 shows that anilinogeranyl incorporation into proteins begins within two hours of incubation with AGOH and is therefore competitive with the endogenous pools of FPP. This demonstrate that intracellular concentrations of AGPP can be achieved that are high enough to compete with the endogenous pool of FPP for FTase dependent transfer to proteins.

Referring again to FIG. 12, a number of proteins with molecular weights ranging from 30-70 kDa are modified with the anilnogeranyl moiety. However, protein bands for Ras and other normally farnesylated small molecular weight GTPases in the 19-27 kDa range are conspicuously absent. Previous reports have shown that the majority of small molecular weight GTPases are normally geranylgeranylated and that the farnesylated small molecular weight GTPases are present in relatively low abundance. Consequently, the farnesylated small molecular weight GTPases are difficult to detect and only faint bands corresponding to these molecules are found when tritium labeled farnesol is incubated with glioma cells (C6) or green monkey kidney cells (CV-1). Determination of Ras prenylation status is an important assay in the evaluation of FTI efficacy and is most often carried out by metabolic labeling with $^3$H-mevalonate. Extracts of cells overexpressing a GST-Ras fusion protein grown in the presence of AGOH with the Anti-AG to overcome the low natural levels of endogenous Ras are probed. HEK-293 cells are transiently transfected with a vector expressing glutathione S-transferase (GST) tagged wild type H-Ras. The cells are then incubated with AGOH, lysed, analyzed by SDS-PAGE and probed with primary antibodies to the GST-tag and to the Anti-AG modification.

Figure 15:
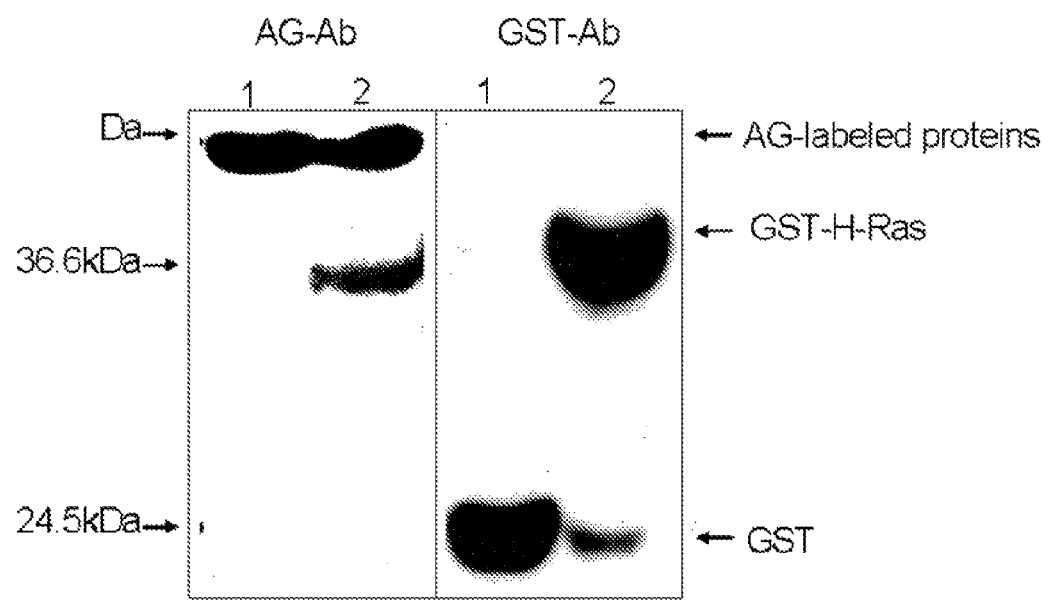
FIG. 15 depicts the results of a study wherein cells overexpressing Ras are incubated with lovostatin and geranylgeranyl alcohol, then treated with anilinogeranyl alcohol in the absence of lovostatin before extracting the cellular proteins, running the samples on an SDS-PAGE gel analyzed by western blot with an Anti-GST antibody or Anti-AG antibody, wherein lane 1 includes control cells without Ras overexpression and lane 2 contains cells over-expressing Ras.

FIG. 15 shows a representative blot in which anilnogeranyl group is incorporated into the GST-tagged Ras protein and other higher molecular weight proteins. These results suggest that anilinogeranyl modified Ras is present in cells not over expressing GST-Ras at concentrations below the level of detection possible with this AB.

Example 2

Procedures

General

All RP-HPLC is performed on an Agilent 1100 HPLC system equipped with a microplate autosampler, diode array and fluorescence detector. The HPLC analysis is performed with a vydac C4 column with 0.01% TFA in water (A) and 0.01% TFA CH3CN (B) as the mobile phase. Peptides are purchased from peptidogenics and each contained a dansyl group N linked to a glycine linker followed by a C residue then a variable aaX sequence (VIL or VIM). Spectrofluorometric analyses are performed in a 96-well flat bottom., non-binding surface, black polystyrene plate (Excitation wavelength, 340 nm; emission wavelength 505 nm with a 10 nm cutoff). The plate reader is a SpectraMax GEMINI XPS fluorescence well-plate reader. Absorbance readings are determined using a Cary UV/Vis spectrophotometer.

Steady-state Peptide Kinetics

The kinetic constants $K_m^{peptide}$ and $k_{cat}$ with GGPP, and the analogs with each peptide are determined in triplicate measurements using a continuous spectrofluorometric assay adapted for a 96-well plate. The following assay components are assembled in individual wells of a 96-well plate and incubated at 30° C. for 20 minutes: 180 μL of assay butler (52 mM Tris-HCl, 12 mM MgCl2, 12 μM ZnCl2 pH 7.4), 40 μL of detergent (0.125% n-dodecyl-β-D-maltoside in assay buffer), 40 μL of reducing agent (50 mM DTT in assay buffer) 20 μL of GGPP or analog (200 μM in 25 mM NH4HCO3) and 20 μL of N-dansyl-GCaaX peptide (variable concentration). Fluorescence is detected using a time based scan at 30° C. for 120 minutes. The velocity of each reaction is determined by converting the rate of increase in fluorescence intensity units (FLU/s) to μM/s with equation 1.

$$v_i = (R \cdot P)/(F_{MAX} - F_{MIN}) \qquad \text{Equation 1}$$

Where $v_i$ is the velocity of the reaction in μM/s. R is the rate of the reaction in FLU/s. P is equal to the concentration of modified product in μM (see below). $F_{MAX}$ is the fluorescence intensity of fully modified product. $F_{MIN}$ is the fluorescence of a reaction mixture that contained 20 μL of assay buffer in the place of GGTaseI. Complete modification of peptides is assumed when fluorescence stabilized for more than 10 minutes and is confirmed by RP-HPLC analysis of the reaction mixture.

Final analysis peptide concentrations are chosen based on preliminary determination of the $Km^{peptide}$ with 0.5, 1, 5 and 10 μM dansyl-GCaaX concentrations (see below). The final analysis used 8 peptide concentrations which are: ⅙, ⅕, ¼, ½, ¾, 1, 2, and 3 times the estimated $Km^{peptide}$. The reaction is then initiated by the addition of 20 μL of GGTaseI (final 10 nM). Fluorescence enhancement is determined as described above.

Complete modification of peptides is assumed when fluorescence stabilized for more than 10 minutes and is confirmed by RP-HPLC analysis of the reaction mixture. If the reactions that contained higher concentrations of peptides did not go to completion the Fmax-Fmin value is extrapolated using a linear plot of the $F_{max} - F_{min}$ for each of the lower concentration reactions that did go to completion. Alternatively the extent of input peptide modified is determined by RP-HPLC analysis of the dansyl moiety peak absorbance corresponding to the unmodified and modified peptides. The percent of modified peptide relative to the total input peptide is used to calculate the concentration of product in the mixture.

The velocities of the reactions are plotted against the concentration of peptide and are fit to the Michaelis-Menten equation (Equation 2) to give the apparent $k_{cat}$ (app$k_{cat}$) and $Km^{peptide}$ (appKmpeptide) values. Where et is the total enzyme concentration and [Pep] is the total input peptide. The $k_{cat}/Km^{peptide}$ value is derived from a Lineweaver-Burke plot of the same data points.

$$v_i/e_i = (appk_{cat}*[Pep])/(appKm^{peptide}+[Pep]) \quad \text{Equation 2}$$

Peptide Competition

Competition reactions are prepared with the same components given for the $k_{cat}/Km^{peptide}$ analysis except two peptides are added to the mixture at a single concentration. Peptides A and B are diluted to 45 µM in Tris-HCl buffer (pH=7.4) and the concentration checked by reading the Abs of the solution at 340 nm ($\epsilon^{dansyl}$=4250 Abs·$M^{-1}$·$cm^{-1}$). 20 µL of peptide A and 20 µL of peptide B are then added to reaction mixtures as described above except only 160 µL of assay buffer is added. Separate reactions are prepared as a standard with GGPP or the analogs and only one peptide as described above. The reactions are then initiated with the addition of GGTaseI (10 nM final concentration) and analyzed spectrofluorometrically. The reactions are stopped prior to consumption of more than 50% of either peptide by adding 20 µL of a stop solution (isopropyl alcohol and acetic acid 8:2). HPLC analysis is then performed with 100 µL of the reaction mixture loaded onto C18 column and eluted with a linear gradient of 0-20 min 50% B to 100% B at a flow rate of 1 mL/min. Peaks on the 340 nm trace chromatogram that correspond to both the standard reactions and fluorescent peaks are then integrated. The ratios of products are calculated according to Equation 3.

$$(I_{Amod}/I_{Atot})/(I_{Bmod}/I_{Btot}) \quad \text{Equation 3}$$

Where $I_{Amod}$ is the integral of the modified peptide A, $I_{Atot}$ is the integral of the modified peptide A plus the unmodified peptide A, $I_{Bmod}$ is the integral of the modified peptide B and $I_{Btot}$ is the integral of the modified peptide B plus the unmodified peptide B. Alternatively, the ratios are calculated using the integrals of the standard peptides fluorescence relative to competition product fluorescence giving less than a 5% difference in the calculated ratio.

GGPP Competition

Competition reactions are prepared with the same components given for the $k_{cat}/Km^{peptide}$ analysis except two isoprenoids are added to the mixture and the peptide concentration is held constant. GGPP and the analog are diluted to 200 µM in 25 mM $NH_4HCO_3$. 20 µL of GGPP and 20 µL of analog are then added to a 260 µL solution of peptide, DTT and detergent in 52 mM Tris-HCl buffer pH=7.4 (final concentrations DTT=6.7 mM, DM=0.033%, Peptide=3 µM, analog=13 µM and FPP=13 µM). The concentration of peptide is determined by absorbance of the dansyl group and isoprenoid diphosphate concentrations are determined using absorbance and the extinction coefficient of N-Methyl-aniline (9120 Abs·$M^{-1}$·$cm^{-1}$) and N-methyl-p-$NO_2$aniline (18,430 Abs·$M^{-1}$·$cm^{-1}$). The reactions are initiated with the addition of FTase and analyzed spectrofluorometrically (20 nM final GGTaseI concentration). The reactions are stopped after 2 hours with a mixture of acetic acid and iPrOH. HPLC analysis is then performed with 100 µL of the reaction mixture loaded onto C18 column and eluted with a linear gradient of 0-20 min 50% B to 100% B at a flow rate of 1 mL/min. Peaks on the 340 nm trace chromatogram that corresponded to standard reaction fluorescent peaks are then integrated. The ratios of products are calculated using $I_{analog}/I_{FPP}$, where $I_{analog}$ is the integral of the peptide modified with the analog and $I_{FPP}$ is the integral of the peptide modified with FPP.

GGTaseI Protein Substrate Modification

3 µM recombinant bacterially expressed H-Ras is incubated with 10 µM AFPP or NAFPP and 1 µM FTase in 300 µL of Tris-HCl buffer (pH=7.4) The reactions are incubated for 30 min at 37° C., boiled with SDS and PAGE performed using 10 µL of the reaction mixtures.

AFOH Incorporation Into Unblocked Cells

Plates are coated with poly-L-Lysine and seeded with in Dulbecco's modified Eagle's medium with 5% fetal bovine serum. The cells are then treated with DMSO as a vehicle, or 30 µM AFOH is added and incubated at 37° C. overnight. Medium is then removed and cells are extracted into 500 µL of RIPA buffer containing Protease Inhibitor cocktail I (calbiochem). The supernatant is removed and used for western blotting.

Western Blot Analysis

Protein concentration is determined using a Bradford reagent kit (Pierce) with 1:100 dilutions of the cell lysates. The proteins from the GGTaseI reaction mixtures or cell lysates are then separated using 12% SDS-polyacrylamide gels followed by transfer to nitrocellulose membranes. The membranes are incubated in blocking buffer PBS Casein and Tween buffer for one hour at room temperature, after which the following sequential steps are used: incubation with anti-AG or anti-NAG to 1:10,000 in PCT for one hour; 3×15 minute washes with vigorous shaking in PBS Tween buffer; incubation at room temperature one hour with goat anti-rabbit horseradish peroxidase-conjugated secondary antibody (Zymed) at a dilution of 1:20,000 in PCT buffer; and four 15 minute washes with PT buffer. The membranes are then subjected to enhanced chemiluminescene detection by incubation in 20 mL of detection buffer (Pierce Super Signal) for one minute.

Scheme 2: Synthesis of AFPP and NAFPP

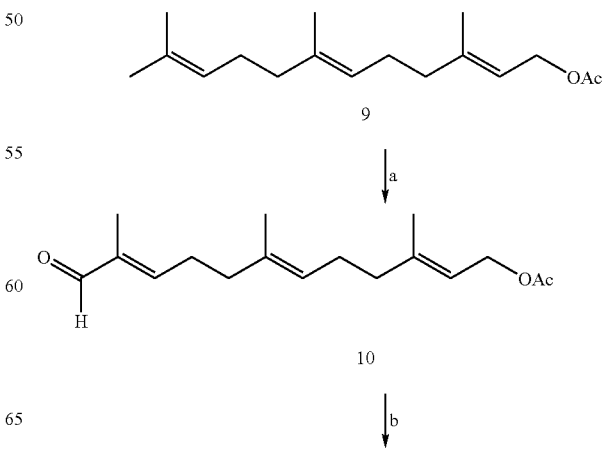

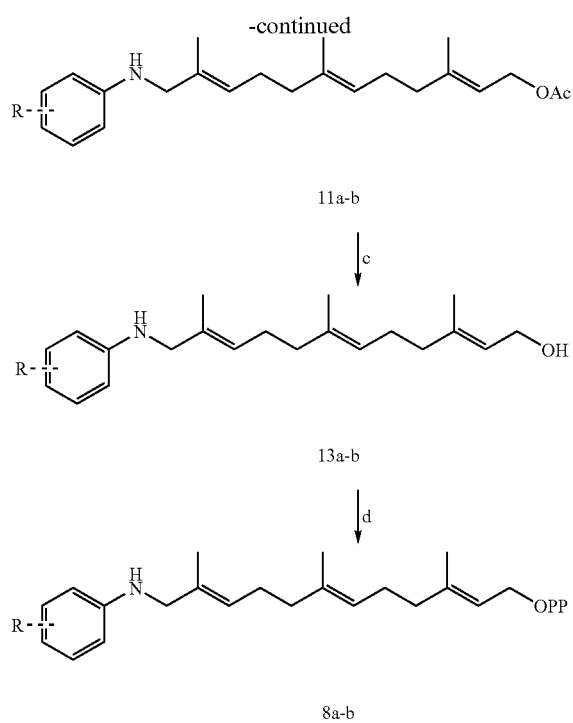

-continued 11a-b 13a-b 8a-b

Reagents:
(a) SeO₂ DCM 2 hrs 0° C.;
(b) aniline 12a-b HOAc, NaBH(OAc)₃, DCE, rt;
(c) K₂CO₃ MeOH/Water;
(d) PPh₃Cl₂, MeCN, rt; 10 minutes ((nBu)₄N)₃HP₂O₇, MeCN overnight.

Reference is made herein to the synthesis set forth in Scheme 2, and to the compounds contained in Scheme 1, identified by the numerals 8a-13b.

Example 2

Results

Synthesis of Geranylgeranyl Diphosphate Analogs with Substituted Aniline Moiety

The synthetic route shown in Scheme 2 is analogous to the synthesis of AGPP (shown in Scheme 1) with farnesyl acetate 9 as the starting material rather than geranyl acetate. The SeO² oxidation of farnesyl acetate 9 is less efficient than geranyl acetate giving lower yields then when the same conditions are used with geranyl acetate. The yield of the reaction is increased when using ethereal co-solvents, which are believed to stabilize stabilizing the transition state with SeO₂. Following farnesyl acetate oxidation to the α,β-unsaturated aldehyde 10 the aniline moiety is incorporated by reductive amination followed by saponification to give the alcohols 13a (AFOH) and 13b (NAFOH). The alcohols are then halogenated and converted to diphosphate, as previously described for the AGPP series of FPP analogs giving AFPP 8a and NAFPP 8b. This route provides a convenient method for the incorporation of a wide variety of aniline functionalities into the geranylgeranyl diphosphate skeleton.

AFPP and NAFPP are Transferable GGTaseI Substrates

Figure 16:
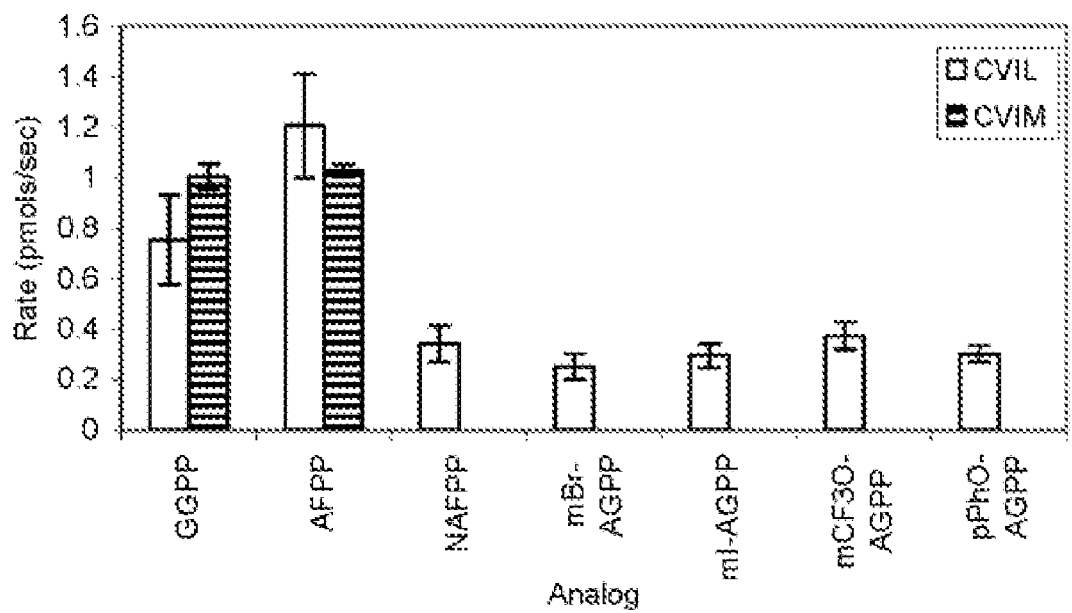
FIG. 16 depicts the results of a study wherein proteins are mixed with various unnatural substrates of the present invention, a reaction is initiated by adding GGTaseI, and reaction rates are calculated.

In order to determine whether the anilinofarnesyl diphosphate analogs are substrates for the GGTaseI enzyme the transfer rate of the analogs is measured with two dansylated-GCaaX peptide substrates for GGTaseI as described in these examples with the FTase enzyme. In addition the entire AGPP analog library from these examples is screened to see if any of the AGPP analogs are also substrates for GGTaseI. The peptides correspond to a canonical GGTaseI substrate peptide (CVIL) and a peptide that is a substrate for both FTase and GGTaseI (CVIM). GGPP is confirmed to be a substrate with the CVIM and CVIL peptides. It is found that AFPP and NAFPP are both substrates for GGTaseI. In addition it is found that several of the meta-substituted AGPP analogs can behave as substrates for GGTaseI The reaction rate of the analogs that are substrates for GGTaseI are shown in FIG. 16. It is found that none of the AGPP analogs or NAFPP are substrates for GGTaseI when CVIM is the target, but are substrates when CVIL is the target. This suggests that the interactions of the CVIM peptide differ from those of the CVIL peptide in the GGTaseI active site.

AFPP and NAFPP are Recognized by Anti-AG and Anti-NAG Antibodies

Figure 17A:
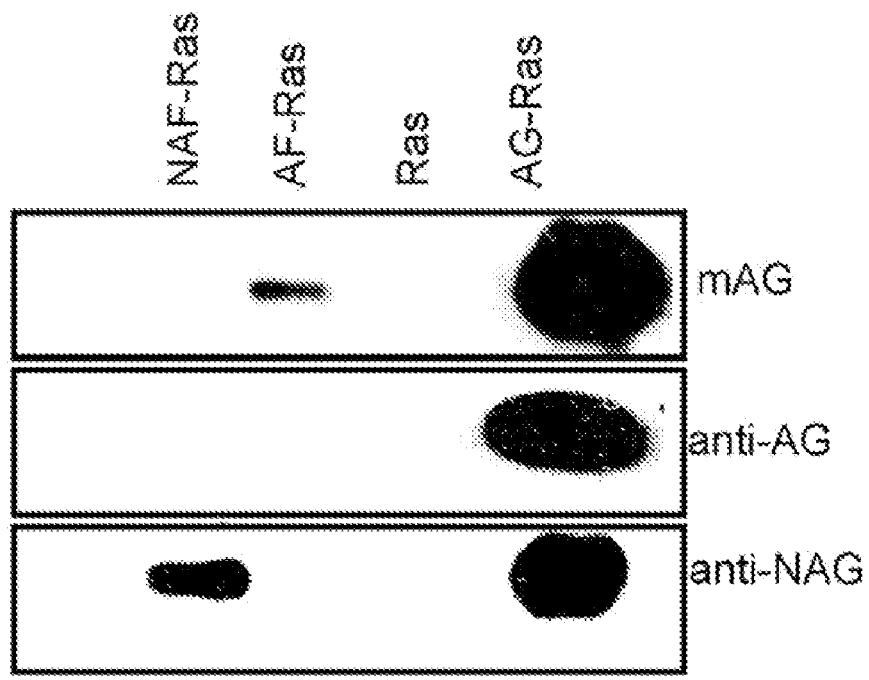
FIG. 17A depicts the results of a Western analysis of anilinofarnesylated and nitroanilinofarnesylated proteins probed with mAG, Anti-AG and Anti-NAG.

AGPP as an unnatural probe for the modification of proteins is useful to determine the cellular prenylation status of proteins and for confirming the in vitro modification of proteins by FTase. Antibodies specific for the anilinogeranyl (Anti-AG) and pNO₂-anilinogeranyl (Anti-NAG) modification of proteins are specific for the aniline isoprenoid of the modified protein. In order to determine whether the antibodies can detect anilinofarnesylated or pNO₂-anilinofarnesylated proteins proteins modified with the AFPP analogs are prepared. Using a relatively large amount of GGTaseI, bacterially expressed H-Ras proteins modified in vitro with the AFPP and NAFPP analogs can be obtained. With reference to FIG. 17A, Western blot analysis of the reaction mixtures indicates that the analog is incorporated into the protein and that the antibodies specifically detect the anilinofarnesylated and pNO₂-anilinofarnesylated proteins. The Anti-AG antibody is unable to detect the anilinofarnesylated protein. However, a mouse monoclonal antibody raised against the same hapten is able to detect the modified protein.

Cell Labeling with AFOH

Figure 17B:
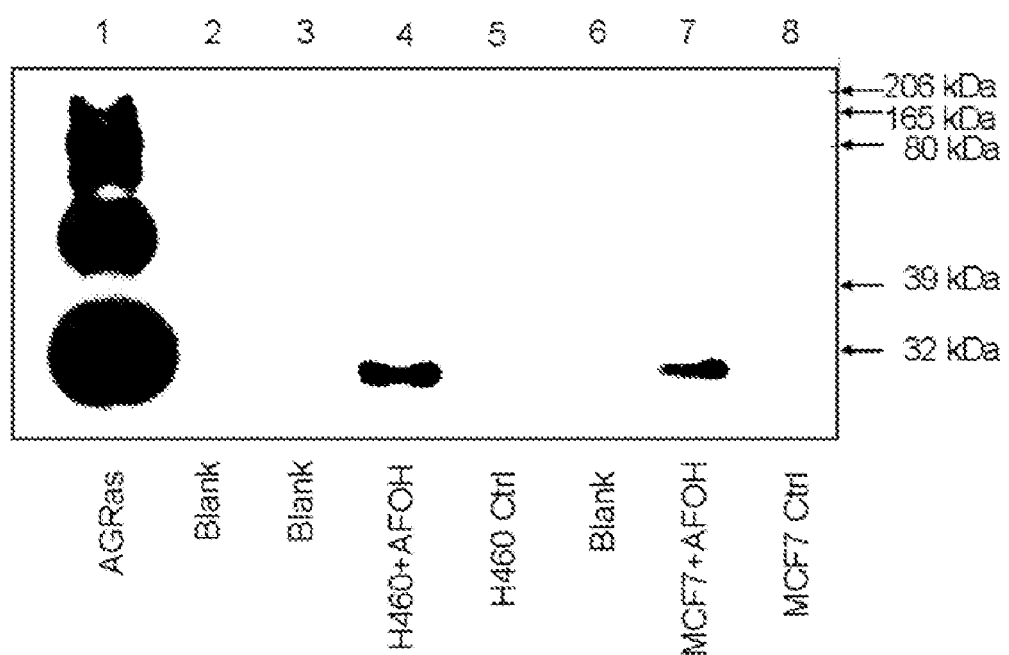
FIG. 17B depicts the results of a Western analysis of protein extracted from cells incubated with anilinofarnesyl alcohol, lysed, and run on an SDS-PAGE gel.

Since the anilinofarnesylated proteins can be detected by the anti-AG antibodies, it is then determined whether they can be used to label cellular proteins. To test this, H460 (lung cancer cell line) and MCF7 (breast cancer cell line) cells are treated with the AFOH analog or DMSO, and the cells are lysed and analyzed for AFOH incorporation into proteins. With reference to FIG. 17B, the anti-AG antibody do not appear to label a large number of proteins, but AFOH does appear to be incorporated into proteins with a molecular weight around that of the small molecular weight GTPases. Small molecular weight GTPases are most commonly geranylgeranylated which is consistent with these results. Low detection of labeled proteins may be due to poor detection by the anti-AG antibody for AF modified proteins, or decreased ability of the AFOH due be converted to diphosphate and compete with endogenous GGPP.

It will be evident to those skilled in the art that further modifications can be made to the embodiments described herein without departing from the spirit and scope of the present invention. One of ordinary skill in the art will also recognize that additional embodiments are possible without departing from the teachings of the present invention or the scope of the claims which follow. This detailed description, and particularly the specific details of the exemplary embodiment disclosed therein, is given primarily for clarity of understanding, and no unnecessary limitations are to be understood therefrom, for modifications will become evident to those skilled in the art upon reading this disclosure and can be made without departing from the spirit or scope of the claimed invention.

Throughout this application, various publications are referenced. All such references are incorporated herein by reference. Also incorporated by reference are the following refrences:

REFERENCES

Adjei, A. A. (2003) An overview of farnesyltransferase inhibitors and their role in lung cancer therapy. Lung Cancer, 41 Suppl 1, S55-62.

Adjei, A. A. (2001) Blocking oncogenic Ras signaling for cancer therapy. J. Natl. Cancer Inst. 93, 1062-74.

Andres, D. A., Crick, D. C., Finlin, B. S., and Waechter, C. J. (1999) Rapid identification of cysteine-linked isoprenyl groups by metabolic labeling with [3H]farnesol and [3H]-geranylgeraniol. Methods Mol. Biol. 116, 107-23.

Andres, D. A., Shao, H., Crick, D. C., and Finlin, B. S. (1997) Expression cloning of a novel farnesylated protein, RDJ2, encoding a DnaJ protein homologue. Arch. Biochem. Biophys. 346, 113-24.

Anwar, K., Nakakuki, K., Shiraishi, T., Naiki, H., Yatani, R., and Inuzuka, M. (1992) Presence of ras oncogene mutations and human papillomavirus DNA in human prostate carcinomas. Cancer Res. 52, 5991-6.

Ashar, H. R., Armstrong, L., James, L. J., Carr, D. M., Gray, K., Taveras, A., Doll, R. J., Bishop, W. R., and Kirschmeier, P. T. (2000) Biological effects and mechanism of action of farnesyltransferase inhibitors. Chem. Res. Toxicol. 13, 949-52.

Baron, R., Fourcade, E., Lajoie-Mazenc, I., Allal, C., Couderc, B., Barbaras, R., Favre, G., Faye, J. C., and Pradines, A. (2000) RhoB prenylation is driven by the three carboxyl-terminal amino acids of the protein: evidenced in vivo by an anti-farnesyl cysteine antibody. Proc. Natl. Acad. Sci. U.S.A. 97, 11626-31.

Berger, T. S., Parandoosh, Z., Perry, B. W., and Stein, R. B. (1992) Interaction of glucocorticoid analogues with the human glucocorticoid receptor. J. Steroid Biochem. Mol. Biol. 41,733-8.

Bergo, M. O., Ambroziak, P., Gregory, C., George, A., Otto, J. C., Kim, E., Nagase, H., Casey, P. J., Balmain, A., and Young, S. G. (2002) Absence of the CAAX endoprotease Rcel: effects on cell growth and transformation. Mol. Cell Biol. 22, 171-81.

Berndt, P., Fields, G. B., and Tirrell, M. (1995) Synthetic Lipidation of Peptides and Amino Acids: Monolayer Structure and Properties. J. Am. Chem. Soc. 117, 9515-9522.

Caplin, B, E., Ohya, Y., and Marshall, M. S. (1998) Amino acid residues that define both the isoprenoid and CAAX preferences of the *Saccharomyces cerevisiae* protein farnesyltransferase. Creating the perfect farnesyltransferase. J. Biol. Chem. 273, 9472-9.

Chehade, K. A., Andres, D. A., Morimoto, H., and Spielmann, H. P. (2000) Design and synthesis of a transferable farnesyl pyrophosphate analogue to Ras by protein farnesyltransferase. J. Org. Chem. 65, 3027-33.

Chehade, K. A., Kiegiel, K., Isaacs, R. J., Pickett, J. S., Bowers, K. E., Fierke, C. A., Andres, D. A., and Spielmann, H. P. (2002) Photoaffinity analogues of farnesyl pyrophosphate transferable by protein farnesyl transferase. J. Am. Chem. Soc. 124, 8206-19.

Chehade, K. A. H., Andres, D, A., Morimoto, H., and Spielmann, H. P. (2000) Design and Synthesis of a Transferable Farnesyl Pyrophosphate. J. Org. Chem. 65, 3207-3033.

Chen, X., Yano, Y., Hasuma, T., Yoshimata, T., Yinna, W., and Otani, S. (1999) Inhibition of farnesyl protein transferase and P21ras memebrane association by d-limonene in human pancreas tumor cells in vitro. Chin. Med. Sci. J. 14, 138-44.

Cox, A. D. (2001) Farnesyltransferase inhibitors: potential role in the treatment of cancer. Drugs 61, 723-32.

Crespo, N. C., Ohkanda, J., Yen, T. J., Hamilton, A. D., and Sebti, S. M. (2001) The farnesyltransferase inhibitor, FTI-2153, blocks bipolar spindle formation and chromosome alignment and causes prometaphase accumulation during mitosis of human lung cancer cells. J. Biol. Chem. 276, 16161-7.

Crick, D. C., et al., (1998) Geranyl geraniol overcomes the block of cell proliferation by lovastatin in C6 glioma cells. J. Med. Chem. 38(8), 1372-9.

Crick, D. C., Andres, D. A., and Waechter, C. J. (1997) Novel salvage pathway utilizing farnesol and geranylgeraniol for protein isoprenylation. Biochem. Biophys. Res. Commun. 237, 483-7.

Crick, D. C., Andres, D. A., and Waechter, C. J. (1995) Farnesol is utilized for protein isoprenylation and the biosynthesis of cholesterol in mammalian cells. Biochem. Biophys. Res. Commun. 211, 590-9.

Danesi, R., McLellan, C. A., and Myers, C. E., (1995) Specific Labeling of Isoprenylated Proteins: Application to Study Inhibitors of the Post-Translational Farnesylation and Geranylgeraniolation. Biochm. Biophys. Res. Comm., 206 (2), 637-43.

Davisson, V. J., Woodside, A. B., Neal, T. R., Stremler, K. E., Muehlbacher, M., and Poulter, C. D. (1986) Phosphorylation of Isoprenoid Alcohols. J. Org. Chem. 51, 4768-4779.

Dickson, J. K., Jr., et al., (1996) Orally active squalene synthase inhibitors: bis((acyloxy)alkyl) prodrugs of the alpha-phosphonosulfonic acid moiety. J. Med. Chem., 39(3), 661-4.

Dunten, P., Kammlott, U., Crowther, R., Weber, D., Palermo, R., and Birktoft, J. (1998) Protein Farnesyltransferase: Structure and Implications for Substrate Binding. Biochemistry 37, 7907-7912.

Dursina, B., et al., (2006) Identification and specificity profiling of protein prenyltransferase inhibitors using new fluorescent phosphoisoprenoids. J. Am. Chem. Soc. 128(9), 2822-35.

Eummer, J. T., et at. (1999) Novel Limonene Phosphate and Farnesyl Diphosphate Analogues: Design, Synthesis, and Evaluation as Potential Protein-Farnesyl Transferase Inhibitors. Biorg. and Med. Chem., 7, 241-50.

Fiordalisi, J. J., Johnson, R. L., 2nd, Weinbaum, C. A., Sakabe, K., Chen, Z., Casey, P. J., and Cox, A. D. (2003) High affinity for farnesyltransferase and alternative prenylation contribute individually to K-Ras4B resistance to farnesyltransferase inhibitors. J. Biol. Chem. 278, 41718-27.

Gibbs, B. S., Zahn, T. J., Mu, Y., Sebolt-Leopold, J. S., and Gibbs, R. A. (1999) Novel Farnesol and Geranylgeraniol Analogues: A Potential New Class of Anticancer Agents Directed against Protein Prenylation. J. Med. Chem. 42, 3800-3808.

Gronborg, M., Kristiansen, T. Z., Stensballe, A., Andersen, J. S., Ohara, O., Mann, M., Jensen, O. N., and Pandey, A. (2002) A mass spectrometry-based proteomic approach for identification of serine/threonine-phosphorylated proteins by enrichment with phospho-specific antibodies: identification of a novel protein, Frigg, as a protein kinase A substrate. Mol. Cell Proteomics 1, 517-27.

Habeeb, A. F. S. A. (1966) Determination of free amino groups in protien by trinitrobenzene sulfonic acid. Anal. Biochem. 14, 328.

Holstein, S. A., Wohlford-Lenane, C. L., Wiemer, D. F., and Hohl, R. J. (2003) Isoprenoid Pyrophosphate Analogues Regulate Expression of Ras-Related Proteins. Biochemistry 42, 4384-4391.

Kho, Y., Kim, S. C., Jiang, C., Barma, D., Kwon, S. W., Cheng, J., Jaunbergs, J., Weinbaum, C., Tamanoi, F., Falck, J., and Zhao, Y. (2004) A tagging-via-substrate technology for detection and proteomics of farnesylated proteins. Proc. Natl. Acad. Sci. U.S.A. 101, 12479-84.

Kim, K. W., et al., (2001) Inactivation of farnesyltransferase and geranylgeranyl-transferase I by caspase-3: cleavage of the common alpha subunit during apoptosis. Oncogene. 20(3), 358-66.

Konishi, N., Hiasa, Y., Tsuzuki, T., Tao, M., Enomoto, T., and Miller, G. J. (1997) Comparison of ras activation in prostate carcinoma in Japanese and American men. Prostate 30, 53-7.

Konishi, N., Hiasa, Y., Matsuda, H., Tao, M., Tsuzuki, T., Hayashi, I., Kitahori, Y., Shiraishi, T., Yatani, R., Shimazaki, J., and et al. (1995) Intratumor cellular heterogeneity and alterations in ras oncogene and p53 tumor suppressor gene in human prostate carcinoma. Am. J. Pathol. 147, 1112-22.

Lesh, R. E., Emala, C. W., Lee, H. T., Zhu, D., Panettieri, R. A., and Hirshman, C. A. (2001) Inhibition of geranylgeranylation blocks agonist-induced actin reorganization in human airway smooth muscle cells. Am. J. Physiol. Lung Cell Mol. Physiol. 281, L824-31.

Lin, H. P., Hsu, S. C., Wu, J. C., Sheen, I. J., Yan, B. S., and Syu, W. J. (1999) Localization of isoprenylated antigen of hepatitis delta virus by anti-farnesyl antibodies. J. Gen. Virol. 80 (Pt 1), 91-6.

Liu, X. H., Suh, D. Y., Call, J., and Prestwich, G. D. (2004) Antigenic prenylated peptide conjugates and polyclonal antibodies to detect protein prenylation. Bioconjugate Chem. 15, 270-7.

Maltese, W. A. (1990) Posttranslational modification of proteins by isoprenoids in mammalian cells. FASEB J. 4, 3319-28.

McGuire, T. F., and Sebti, S. M. (1997) Geranylgeraniol potentiates lovastatin inhibition of oncogenic H-Ras processing and signaling while preventing cytotoxicity. Oncogene 14, 305-12.

Michaelson, D., Ali, W., Chin, V. K., Bergo, M., Silletti, J., Wright, L., Young, S. G., and Philips, M. (2005) Postprenylation CAAX Processing Is Required for Proper Localization of Ras but Not Rho GTPases. Mol. Biol. Cell 4, 1606-16.

Niemi, R., et al. (2000) Biophosphonate prodrugs: synthesis and in vitro evaluation of alkyl and acyloxymethyl esters of etidronic acid as bioreversible prodrugs of etidronate. Eur. J. Pharm. Sci. 11(2), 173-80.

Niemi, R., et al. (1999) Bisphosphonate prodrugs: synthesis and in vitro evaluation of novel acyloxyalkyl esters of clodronic acid. J Med Chem. 42(24), 5053-8.

Pompliano, D. L., R. P. Gomez, and N. J. Anthony. (1992) Intramolecular Fluorescence Enhancement—a Continuous Assay of Ras Farnesyl-Protein Transferase. Journal of the American Chemical Society. 114(20), 7945-7946.

Quellhorst, G. J., C. M. Allen, and M. Wessling-Resnick, (2001) Modification of Rab5 with a photoactivatable analog of geranylgeranyl diphosphate. J. Biol Chem. 276(44), 40727-40733.

Ramamurthy, V., Roberts, M., van den Akker, F., Niemi, G., Reh, T. A., and Hurley, J. B. (2003) AIPL1, a protein implicated in Leber's congenital amaurosis, interacts with and aids in processing of farnesylated proteins. Proc. Natl. Acad. Sci. U.S.A. 100, 12630-5.

Rawat, D. S., and Gibbs, R. A. (2002) Synthesis of 7-Substituted Farnesyl Diphosphate Analogues. Org. Lett. 4, 3027-3030.

Reid, T. S., and Beese, L. S. (2004) Crystal structures of the anticancer clinical candidates R115777 (Tipifarnib) and BMS-214662 complexed with protein farnesyltransferase suggest a mechanism of FTI selectivity. Biochemistry 43, 6877-84.

Reid, T. S., et al. (2004) Crystallographic analysis of CaaX prenyltransferases complexed with substrates defines rules of protein substrate selectivity. J Mol Biol. 343(2), 417-33.

Roskoski, R., Jr. (2003) Protein prenylation: a pivotal posttranslational process. Biochem. Biophys. Res. Commun. 303, 1-7.

Rowell, C. A., Kowalczyk, J. J., Lewis, M. D., and Garcia, A. M. (1997) Direct demonstration of geranylgeranylation and farnesylation of Ki-Ras in vivo. J. Biol. Chem. 272, 14093-7.

Rowinsky, E. K., Windle, J. J., and Von Hoff, D. D. (1999) Ras protein farnesyltransferase: A strategic target for anticancer therapeutic development. J. Clin. Oncol. 17, 3631-52.

Santucci, R., Mackley, P. A., Sebti, S., and Alsina, M. (2003) Farnesyltransferase inhibitors and their role in the treatment of multiple myeloma. Cancer Control 10, 384-7.

Scheffzek, K., Stephan, L., Ole N. Jensen5, Illenberger, D., and Gierschik, P. (2000) The Rac-RhoGDI complex and the structural basis for the regulation of Rho proteins by RhoGDI. Nat. Struct. Biol. 7, 122-126.

Sebti, S. M., and Hamilton, A. D. (2000) Farnesyltransferase and geranylgeranyltransferase I inhibitors and cancer therapy: lessons from mechanism and bench-to-bedside translational studies. Oncogene 19, 6584-93.

Serafinowska, H. T., et al. (1995) Synthesis and in vivo evaluation of prodrugs of 9-[2-(phosphonomethoxy)ethoxy] adenine. J. Med. Chem. 38(8), 1372-9.

Shaw, J. P., et al., (1997) Metabolism and pharmacokinetics of novel oral prodrugs of 9-[(R)-2-(phosphonomethoxy) propyl]adenine (PMPA) in dogs. Pharm Res. 14(12), 1824-9.

Shi, G. X., and Andres, D. A. (2005) Rit contributes to nerve growth factor-induced neuronal differentiation via activation of B-Raf-extracellular signal-regulated kinase and p38 mitogen-activated protein kinase cascades. Mol. Cell Biol. 25, 830-46.

Shi, Y., Wu, J., Mick, R., Cerniglia, G. J., Cohen-Jonathan, E., Rhim, J. S., Koch, C. J., and Bernhard, E. J. (2005) Farnesyltransferase inhibitor effects on prostate tumor microenvironment and radiation survival. Prostate 62, 69-82.

Thai, L., Rush, J. S., Maul, J. E., Devarenne, T., Rodgers, D. L., Chappell, J., and Waechter, C. J. (1999) Farnesol is utilized for isoprenoid biosynthesis in plant cells via farnesyl pyrophosphate formed by successive monophosphorylation reactions. Proc. Natl. Acad. Sci. U.S.A. 96, 13080-5.

Troutman J. M., Chehade, K. A., Kiegiel, K., Andres, D. A., Speilmann, H. P. (2004) Synthesis of acyloxymethyl ester prodrugs of the transferable protein farnesyl transferase substrate farnesyl methylenediphosphonate. Bioorg Med chem. Lett. 14 (19), 4979-82.

Troutman, J. M., Roberts, M. J., Andres, D. A., Spielmann, H. P. (2005) Tools to analyze protein farnesylation in cells. Bioconjug Chem. 16(5), 1209-17.

Turek-Etienne, T. C., Strickland, C. L., and Distefano, M. D. (2003) Biochemical and Structural Studies with Prenyl Diphosphate Analogues Provide Insights into Isoprenoid Recognition by Protein Farnesyl Transferase. Biochemistry 42, 3716-3724.

Vepsalainen, J. J. (1999) Bisphosphonate prodrugs: a new synthetic strategy to tetraacyloxymethyl esters of methylenebisphosphonates. Tetrahedron Lett. 40, 8491-8493.

Vergnes, L., Peterfy, M., Bergo, M. O., Young, S. G., and Reue, K. (2004) Lamin B1 is required for mouse development and nuclear integrity. Proc. Natl. Acad. Sci. U.S.A. 101, 10428-33.

Watanabe, M., Shiraishi, T., Yatani, R., Nomura, A. M., and Stemmermann, G. N. (1994) International comparison on ras gene mutations in latent prostate carcinoma. Int. J. Cancer 58, 174-8.

Whyte, D. B., Kirschmeier, P., Hockenberry, T. N., Nunez-Oliva, I., James, L., Catino, J. J., Bishop, W. R., and Pai, J. K. (1997) K- and N-Ras are geranylgeranylated in cells treated with farnesyl protein transferase inhibitors. J. Biol. Chem. 272, 14459-64.

Yang, G. J. C., Arakawa-Uramoto, H., Wang, X., M. A. Gawinowicz, Zhao, K., and Landry, D. W. (1996) Anti-Cocaine Catalytic Antibodies: A Synthetic Approach to Improved Antibody Diversity. J. Am. Chem. Soc. 118, 5881-5890.

Yuan, L. C., T. C. Dahl, and R. Oliyai (2001) Degradation kinetics of oxycarbonyloxymethyl prodrugs of phosphonates in solution. Pharm Res. 18(2), 234-7.

Zhang, F. L., and Casey, P. J. (1996) Protein prenylation: molecular mechanisms and functional consequences. Annu. Rev. Biochem. 65, 241-69.

Zhu, K., Hamilton, A. D., and Sebti, S. M. (2003) Farnesyltransferase inhibitors as anticancer agents: current status. Curr. Opin. Investig. Drugs 4, 1428-35.

What is claimed is:

1. An isolated antibody that recognizes a unique moiety of a protein modified therewith, the unique moiety being selected from the group consisting of: para-nitro-anilinogeranyl moiety, ortho-fluoro-anilinogeranyl moiety, para-cyano-anilinogeranyl moiety, para-nitro-anilinofarnesyl moiety, meta-cyano-anilinogeranyl moiety, and para-bromo-anilinogeranyl moiety, wherein the antibody that recognizes the unique moiety of the modified protein does not recognize farnesylated proteins or geranylgeranylated proteins.

2. An isolated antibody that recognizes a unique moiety of a protein modified therewith, the unique moiety being selected from the group consisting of: anilinogeranyl moiety, para-fluoro-anilinogeraniol moiety, meta-fluoro-anilinogeranyl moiety, para-methyl-anilinogeranyl moiety, meta-methyl-anilinogeranyl moiety, and meta-bromo-anilinogeranyl moiety, wherein the antibody that recognizes the unique moiety of the modified protein does not recognize farnesylated proteins or geranylgeranylated proteins.

3. The isolated antibody according to claim 2, wherein the unique moiety is an anilinogeranyl moiety.

4. The isolated antibody according to claim 3, wherein the the unique moiety is an anilinogeranyl moiety of anilinogeranyl diphosphate, or an anilinogeranyl moiety of anilinogeranyl alcohol.

5. An isolated monoclonal antibody that recognizes an anilinofarnesyl moiety of a protein modified therewith, wherein the antibody that recognizes the unique moiety of the modified protein does not recognize farnesylated proteins or geranylgeranylated proteins.

6. The isolated antibody according to claim 1, wherein the unique moiety is a $pNO_2$-anilinogeranyl moiety.

7. The isolated antibody according to claim 6, wherein the unique moiety is a $pNO_2$-anilinogeranyl moiety of $pNO_2$-8-anilinogeranyl diphosphate, or a $pNO_2$-anilinogeranyl moiety of $pNO_2$-8-anilinogeranyl alcohol.

8. The isolated antibody according to claim 1, wherein the unique moiety is a para-cyano-anilinogeranyl moiety or para-notro-anilinofarnesyl moiety.

9. The isolated antibody according to claim 1, wherein the antibody is an isolated monoclonal antibody, wherein the unique moiety is a para-nitro-anilinogeranyl moiety.

10. The isolated monoclonal antibody according to claim 9, wherein the antibody recognizes an anilinogeranyl moiety of a protein modified with the anilinogeranyl moiety.

\* \* \* \* \*